(12) United States Patent
Barnea et al.

(10) Patent No.: US 11,565,091 B2
(45) Date of Patent: Jan. 31, 2023

(54) INTRACRANIAL VOLUME ADAPTOR FOR CEREBRAL BLOOD FLOW

(71) Applicants: Ramot at Tel-Aviv University Ltd., Tel-Aviv (IL); Tel HaShomer Medical Research Infrastructure and Services Ltd., Ramat-Gan (IL); Hadasit Medical Research Services and Development Ltd., Jerusalem (IL)

(72) Inventors: Ofer Barnea, Herzlia (IL); Omer Doron, Holon (IL)

(73) Assignees: Ramot at Tel-Aviv University Ltd., Tel-Aviv (IL); Tel HaShomer Medical Research Infrastructare and Services Ltd., Ramat-Gan (IL); Hadasit Medical Research Services and Development Ltd., Jerusalem (IL)

( * ) Notice: Subject to any disclaimer, the term of this patent is extended or adjusted under 35 U.S.C. 154(b) by 768 days.

(21) Appl. No.: 16/461,383

(22) PCT Filed: Nov. 16, 2017

(86) PCT No.: PCT/IL2017/051255
§ 371 (c)(1),
(2) Date: May 16, 2019

(87) PCT Pub. No.: WO2018/092139
PCT Pub. Date: May 24, 2018

(65) Prior Publication Data
US 2020/0061355 A1    Feb. 27, 2020

Related U.S. Application Data

(60) Provisional application No. 62/422,616, filed on Nov. 16, 2016.

(51) Int. Cl.
*A61M 27/00*    (2006.01)
*A61M 25/10*    (2013.01)
(Continued)

(52) U.S. Cl.
CPC .... *A61M 27/006* (2013.01); *A61M 25/10181* (2013.11); *A61M 25/10184* (2013.11);
(Continued)

(58) Field of Classification Search
CPC ............ A61M 25/1018; A61M 27/006; A61M 25/10181; A61M 25/10184; A61M 2210/0693
See application file for complete search history.

(56) References Cited

U.S. PATENT DOCUMENTS

| | | | |
|---|---|---|---|
| 6,105,582 | A | 8/2000 | Pranevicius et al. |
| 8,956,379 | B2 | 2/2015 | Luciano et al. |

(Continued)

FOREIGN PATENT DOCUMENTS

| | | |
|---|---|---|
| CN | 104434081 | 3/2015 |
| CN | 104825150 | 8/2015 |

(Continued)

OTHER PUBLICATIONS

Notice of Reason(s) for Rejection dated Nov. 30, 2021 From the Japan Patent Office Re. Application No. 2019-525975 and Its Translation Into English. (15 Pages).
(Continued)

*Primary Examiner* — Jenna Zhang

(57) ABSTRACT

A method for influencing cerebral perfusion in a patient by modifying a volume of a volume adaptor introduced into a cerebral ventricle of the patient, the method comprising identifying a timing of a cerebral blood inflow and/or outflow in a cardiac activity of the patient, modifying a volume of the volume adaptor in synchronization to the identified timing of the cerebral blood flow, to an amount sufficient to modify an intracranial pressure in the cerebral ventricle, such that a flow of the cerebral blood flow is enhanced. In some exemplary embodiments of the inven-
(Continued)

tion, the inflation duration of the volume adapter is short relative to the cardiac cycle.

23 Claims, 27 Drawing Sheets

(51) Int. Cl.
*A61M 25/00* (2006.01)
*A61B 5/03* (2006.01)
*A61M 60/122* (2021.01)
*A61M 60/268* (2021.01)

(52) U.S. Cl.
CPC ............ *A61B 5/031* (2013.01); *A61M 60/122* (2021.01); *A61M 60/268* (2021.01); *A61M 2025/0024* (2013.01); *A61M 2025/0039* (2013.01); *A61M 2205/3331* (2013.01); *A61M 2210/0693* (2013.01); *A61M 2230/04* (2013.01)

(56) References Cited

U.S. PATENT DOCUMENTS

| | | | |
|---|---|---|---|
| 2006/0052737 A1 | 3/2006 | Bertrand et al. | |
| 2006/0111659 A1* | 5/2006 | Tyler | |
| 2006/0129203 A1* | 6/2006 | Garabedian | A61N 1/0539 607/139 |
| 2009/0177279 A1* | 7/2009 | Luciano | A61M 60/546 623/11.11 |
| 2010/0318114 A1* | 12/2010 | Pranevicius | A61M 25/10 606/194 |
| 2011/0004158 A1* | 1/2011 | Luciano | A61M 27/002 604/131 |
| 2015/0005800 A1* | 1/2015 | Anile | A61M 29/02 606/192 |
| 2021/0146101 A1 | 5/2021 | Barnea et al. | |

FOREIGN PATENT DOCUMENTS

| | | |
|---|---|---|
| JP | 05-300880 | 11/1993 |
| JP | 2009-502247 | 1/2009 |
| WO | WO 99/01172 | 1/1999 |
| WO | WO 2006/014764 | 2/2006 |
| WO | WO 2018/092139 | 5/2018 |
| WO | WO 2007/014028 | 7/2021 |

OTHER PUBLICATIONS

Notification of Office Action and Search Report dated Dec. 24, 2020 From the State Intellectual Property Office of the People's Republic of China Re. Application No. 201780082609.X and Its Translation of Office Action Into English. (5 Pages).
International Preliminary Report on Patentability dated May 31, 2019 From the International Bureau of WIPO Re. Application No. PCT/IL2017/051255. (10 Pages).
International Search Report and the Written Opinion dated Feb. 26, 2018 From the International Searching Authority Re. Application No. PCT/IL2017/051255. (15 Pages).
Panerai "The Critical Closing Pressure of the Cerebral Circulation", Medical Engineering & Physics 25: 621-632, 2003.
Piechnik et al. "Cerebral Venous Blood Outflow: A Theoretical Model Based on Laboratory Simulation", Neurosurgery, 49(5): 1214-1223, Nov. 2001.
Pranevicius et al. "Cerebral Venous Steal: Blood Flow Diversion With Increased Tissue Pressure", Neurosurgery, 51(5): 1267-1274, Nov. 2002.
Wagshul et al. "The Pulsating Brain: A Review of Experimental and Clinical Studies of Intracranial Pulsatility", Fluids and Barriers of the CNS, 8(5): 1-23, Published Online Jan. 18, 2011.
Examination Report Under Sections 12 & 13 of the Patents Act, 1970 and the Patents Rules, 2003 dated Sep. 15, 2021 From the Government of India, Intellectual Property India, Patents, Designs, Trade Marks, Geographical Indications, The Patent Office Re. Application No. 201927022953. (7 Pages).

\* cited by examiner

INTRACRANIAL VOLUME ADAPTOR FOR CEREBRAL BLOOD FLOW

RELATED APPLICATIONS

This application is a National Phase of PCT Patent Application No. PCT/IL2017/051255 having International filing date of Nov. 16, 2017, which claims the benefit of and priority under 35 USC § 119(e) of U.S. Provisional Patent Application No. 62/422,616 filed on Nov. 16, 2016. The contents of the above applications are all incorporated by reference as if fully set forth herein in their entirety.

FIELD AND BACKGROUND OF THE INVENTION

The present invention, in some embodiments thereof, relates to measuring and/or affecting cerebral blood perfusion and, more particularly, but not exclusively, affecting cerebral blood perfusion through intracranial pressure modification.

U.S. Patent Application No. 2015/0005800 discloses that "the salient feature of device 10 according to the invention is that it measures the intracranial pressure ICP which acts in cerebrospinal fluid CSF during each cardiac cycle of the patient, and determines, on the basis of a specific algorithm and taking account of the measured pressure, the variation in volume of a bag, fitted to implantable device 10 and inserted into a cerebral ventricle of the patient, in order to adapt the CSF pulsation to the requirements of the hydrocephalus syndrome treatment. In particular, device 10 is designed to control the variation in volume of said bag so as to drain a certain amount of cerebrospinal fluid CSF from the cerebral ventricle during the systolic phase, and to return a similar quantity of cerebrospinal fluid CSF to the same cerebral ventricle during the diastolic phase of the cardiac cycle."

U.S. Patent Application No. 2006/0052737 provides "a drainage system that includes a ventricular catheter, a drainage catheter, and a positive displacement pump that can function to actively drain CSF from the ventricles of the brain of a patient."

U.S. Patent Application No. 2010/0318114 discloses "a patient in whom blood diversion due to cerebral venous steal is present, and abolishment of the cerebral venous steal is indicated, is treated by increasing the cerebral venous pressure in the patient. This increase in cerebral venous pressure restores the collapsed cerebral vasculature, thereby increasing cerebral blood flow. The increase in cerebral venous pressure may be achieved using an occluding catheter in the superior vena cava or the internal jugular veins, using external compression of the cervical veins, or any other suitable mechanism. The occlusion may be controlled precisely during treatment, possibly as a function of cerebral blood flow, and after treatment the patient may experience a persistent effect because the cerebral vasculature is no longer collapsed."

U.S. Pat. No. 8,956,379 discloses "devices and systems that alter intracranial compliance, cerebral blood flow and/or intracranial pressure pulsatility/waveform by oscillating the contraction and expansion of a compressible composition within the cranial or spinal cavities such that they increase intracranial capacity. The contraction and expansion of the compressible composition in the oscillating compliance devices can be due to an individual's intracranial pressure, the result of the expansion and compression of a reservoir which is mediated by the contractility of the heart or driven by a pump gaited to a biorhythm. The invention also relates to methods for protecting an individual's brain from abnormal arterial pulsations and for altering an individual's cerebral blood flow using the devices and systems of the invention. The oscillating compliance devices can be used to treat several diseases and/or conditions characterized by altered/abnormal intracranial compliance, cerebral blood flow and/or intracranial pressure pulsatility/waveform, including hydrocephalus, stroke, dementia and migraine headaches, vasospasms, congestive heart failure, cardiopulmonary bypass or carotid endarterectomy."

SUMMARY OF THE INVENTION

Some embodiments of the invention may be exemplified by one or more of the following examples. It is noted that features from one example may be combined with features from another example, to provide additional exemplary embodiments of the invention.

Example 1. A method for influencing cerebral perfusion in a patient by repeatedly modifying a volume of a volume adaptor introduced into a cranial volume of said patient, said method comprising:

estimating a timing or indication thereof of a systolic cerebral blood inflow which forms part of a cerebral blood flow cycle in a cardiac activity of said patient;

shrinking a volume of said volume adaptor to a decreased volume state in synchronization to said estimated timing of said cerebral blood inflow, to an amount sufficient to decrease an intracranial pressure in said cranial volume, such that a flow of said cerebral blood inflow is enhanced; and increasing a volume of said volume adapter to an increased volume state relative to said decreased volume state, wherein said volume is more than 20% higher than a volume at said decreased volume state over less than 30% of said cerebral blood flow cycle.

Example 2. The method according to example 1, further comprising estimating in said cardiac activity of said patient a timing of a cerebral blood outflow, and wherein said increasing is performed in synchronization to said identified timing of said cerebral blood outflow, thereby increasing intracranial pressure in said cranial volume, such that a flow of said cerebral blood outflow is enhanced.

Example 3. The method according to example 1, further comprising estimating in said cardiac activity of said patient a timing of a diastole, and wherein said increasing is performed in synchronization to said diastole to increase venous outflow and followed by a further shrinking so as to increase cerebral perfusion, all in a same cycle.

Example 4. The method according to example 3, wherein said increasing is performed more than ⅓ of said cycle before said decreasing.

Example 5. The method according to example 1, wherein said increasing is performed less than ⅓ of said cycle before said decreasing.

Example 6. The method according to example 1, wherein said shrinking is completed before a time that is 10 ms after said systole starts.

Example 7. The method according to example 2, wherein said increasing is provided in a rate of about 0.05 to about 1 ml/msec.

Example 8. The method according to example 1, wherein said increasing is initiated prior to a timing of a cerebral blood outflow.

Example 9. The method according to example 1, wherein said timing is estimated based on an ECG signal of the patient.

Example 10. The method according to example 1, further comprising monitoring said patient over a period of time of over an hour and detecting physiologic input of said patient by said monitoring and modifying one or both of a degree of said shrinking and a timing of said shrinking according to said physiologic input.

Example 11. The method according to example 1, further comprising monitoring said patient over a period of time of over an hour and detecting physiologic input of said patient by said monitoring and modifying one or both of a degree of said increasing and a timing of said increasing relative to said shrinking according to said physiologic input.

Example 12. The method according to example 10, wherein said detecting physiologic input comprises one or more of CBF, CPP, ICP and integrals, time derivatives and/or composites thereof.

Example 13. The method according to example 1, further comprising introducing said adaptor into said cranial volume and draining a portion of a cerebrospinal fluid from said cranial volume prior to or in a same cycle as an initial increasing in volume of said adaptor.

Example 14. The method according to example 13, wherein said initial increasing comprises increasing over several cycles in synchronization with further removal of fluid.

Example 15. The method according to example 13, wherein said initial increasing comprises increasing during a diastolic portion of said cycle.

Example 16. The method according to any of examples 1-15, comprising determining initial settings for said volume adaptor including both volume and timing.

Example 17. The method of example 16, wherein determining initial timing settings comprises determining a shortest or near shortest delay between said increasing and said decreasing, below which clinical efficacy is significantly compromised.

Example 18. The method according to any of examples 1-15, wherein said volume adaptor has a baseline shrunken volume with at least 1 cc of fluid therein.

Example 19. The method according to any of examples 1-15, wherein said increasing comprises filing with a non-compressible fluid.

Example 20. The method according to any of examples 1-15, wherein said increasing comprises increasing a pressure of a compressible fluid in said expander.

Example 21. A method for influencing cerebral perfusion in a patient by repeatedly modifying a volume of a volume adaptor introduced into a cerebral ventricle of said patient, over several cranial pressure cycles, said method comprising:
estimating a timing of a cerebral blood outflow in a cardiac activity of said patient;
expanding a volume of said volume adaptor in synchronization to said estimated timing of said cerebral blood outflow, to an amount sufficient to increase an intracranial pressure in said cerebral ventricle, such that a flow of said cerebral blood outflow is enhanced, wherein said expansion is over less than 30% of a cerebral blood flow cycle time.

Example 22. The method according to example 21, wherein said expanding is followed by a shrinking of said volume so as to allow perfusion of blood from arteries before an inflow of blood into the brain during systole.

Example 23. The method according to example 21, further comprising estimating in said cardiac activity of said patient a timing of a cerebral blood inflow, and shrinking a volume of said volume adaptor in synchronization to said estimated timing of said cerebral blood inflow, while decreasing intracranial pressure in said cerebral ventricle, such that a flow of said cerebral blood inflow is enhanced.

Example 24. The method according to example 21, wherein said expanding is performed in a first 60% of a diastole of said cycle.

Example 25. The method according to example 21, wherein said expanding is performed in a last 37% of a diastole of said cycle.

Example 26. The method according to example 21, further comprising detecting physiologic input of said patient and determining if to modify a degree and/or timing of said expanding and/or shrinking after said expanding and/or a duration of expansion according to said physiologic input.

Example 27. The method according to example 26, wherein said determining occurs as often as once every 5 minutes.

Example 28. The method according to example 21, wherein said cerebral ventricle is a cerebral spinal fluid space.

Example 29. The method according to example 28, wherein said cerebral ventricle is found in a mechanical influence with at least a portion of an arterial vasculature of said patient.

Example 30. The method according to example 29, wherein said cerebral ventricle is found in a mechanical influence with at least a portion of a venous vasculature of said patient.

Example 31. The method according to example 29, wherein said venous vasculature is bridging veins of said patient.

Example 32. The method according to example 21, wherein said flow of said cerebral blood inflow and/or cerebral blood outflow is enhanced by increasing cerebral blood volume in a range of 5-30%.

Example 33. The method according to example 21, wherein said increasing intracranial pressure is in a range of 2-10%.

Example 34. A system for influencing cerebral perfusion in a brain of a patient, comprising:
a volume adaptor having an expandable compartment sized and shaped to be introduced into a skull of the patient, said volume adaptor operable by switching between a shrunk state sized to significantly decrease intracranial pressure and an expanded state sized to significantly increase intracranial pressure;
at least one sensor for measuring a physiologic output of said patient; and
a processor in operating communication with said volume adaptor, and having instructions for predicting according to said physiologic input a timing of at least one of a cerebral blood inflow and a cerebral diastole; and switching said volume adaptor into said shrunk state in synchronization with said timing of a cerebral inflow, wherein said processor is configured to maintain said adaptor in an non-shrunken state for less than 50% of a duration of a cardiac cycle, said processor configured to apply said switching for at least 100 cardiac cycles our of 1000 consecutive cardiac cycles.

Example 35. The system according to example 34, wherein said processor further comprises instructions for predicting according to said physiologic input a timing of a cerebral blood outflow and switching said volume adaptor into said expanded state in synchronization with said timing of a cerebral outflow.

Example 36. The system according to example 34, comprising a pump operative to switch said adaptor from a shrunk state to an expanded state in less than 50 ms (milliseconds).

Example 37. The system according to example 34, wherein said expandable compartment contains fluid.

Example 38. The system according to example 34, wherein said processor has instructions for controlling an external ventricular drain in conjunction with activating said pump to provide said switch.

Example 39. The system according example 34, wherein said volume adaptor has a maximal volume of between 3 and 6 cc (cubic centimeters).

Example 40. The system according to example 34, further comprising a physiological sensor and wherein said processor has instructions to adjust at least one operating parameter of said pump and/or at least one timing parameter in response to an input from said sensor.

Example 41. The system according to example 40, wherein the controller has instructions to continuously adjust a set of operating parameters of the system in response to patient physiological response.

Example 42. The system according to example 40, wherein the timing parameter comprises an interval between expansion and shrinking and wherein the pump parameter comprises a volume of expansion.

Example 43. The system according to any of examples 34-42, wherein said deformable compartment comprises a non-compliant wall.

Example 44. The system according to any of examples 34-42, wherein controller has instructions to gradually expand said volume adaptor to a first expansion state at times when pressure in said brain is lower.

Example 45. The system according to any of examples 34-42, wherein controller has instructions to automatically identify an initial operation set of parameters by trying out a series of parameter settings.

Example 46. The system according to any of examples 34-42, wherein controller has instructions to automatically generate a pressure volume curve for determining compliance of said brain.

Example 47. A method for influencing cerebral perfusion in a patient by repeatedly modifying a volume of a volume adaptor introduced into a cerebral ventricle of said patient, said method comprising:

estimating a timing of a cerebral blood inflow and/or outflow in a cardiac activity of said patient correlated to a cerebral blood flow cycle;

shrinking and expanding a volume of said volume adaptor, at least twice in a cycle, in synchronization to said timing, to an amount sufficient to modify an intracranial pressure in said cerebral ventricle, such that a flow of said cerebral blood flow is enhanced.

Example 48. A method of controlled volume change in a brain of a patient, comprising:

determining a change or expected change n fluid volume in the brain; and automatically adding or removing fluid in synchronization with said expected change and in a polarity opposite from said change in response to said determining.

Example 49. A method according to example 48, wherein adding is preformed at a diastolic pressure trough of the brain.

Example 50. A method according to example 48, wherein one of said change and said adding or removing is in a compartment sealed off from the brain fluid.

Example 51. A method according to example 48, wherein said synchronization comprises within a same cardiac cycle.

Example 52. A method according to example 48, wherein said change or expected change is manual or natural.

Following are an additional set of examples of some embodiments of the invention.

Example 1. A method for influencing cerebral perfusion in a patient by modifying a volume of a volume adaptor introduced into a cerebral ventricle of the patient, the method comprising: identifying a timing of a cerebral blood inflow in a cardiac activity of the patient; shrinking a volume of the volume adaptor in synchronization to the identified timing of the cerebral blood inflow, to an amount sufficient to decrease an intracranial pressure in the cerebral ventricle, such that a flow of the cerebral blood inflow is enhanced.

Example 2. The method according to example 1, further comprising identifying in the cardiac activity of the patient a timing of a cerebral blood outflow, and expanding a volume of the volume adaptor in synchronization to the identified timing of the cerebral blood outflow, while increasing intracranial pressure in the cerebral ventricle, such that a flow of the cerebral blood outflow is enhanced.

Example 3. The method according to example 2, wherein the expanding is provided in a rate of about 0.5 to about 1.5 ml/sec.

Example 4. The method according to any of examples 2-3, wherein the expanding is initiated prior to a prediction of the timing of a cerebral blood outflow.

Example 5. The method according to any of examples 2-4, wherein the shrinking is initiated prior to a prediction of the timing of a cerebral blood inflow.

Example 6. The method according to any of examples 2-5, further comprising detecting physiologic input of the patient and modifying a degree of the expanding according to the physiologic input.

Example 7. The method according to any of examples 1-5, further comprising detecting physiologic input of the patient and modifying a degree of the shrinking according to the physiologic input.

Example 8. The method according to any of examples 6-7, wherein the modifying the degree of the expanding and/or the degree of the shrinking occurs in a time interval of more than about 5 seconds.

Example 9. The method according to any of examples 6-7, wherein the modifying the degree of the expanding and/or the degree of the shrinking occurs in a time interval of more than about 1 minute.

Example 10. The method according to any of examples 6-9, wherein the detecting physiologic input comprises measuring a cerebral blood flow of the patient.

Example 11. The method according to any of examples 6-10, wherein the detecting physiologic input comprises measuring a cerebral perfusion pressure of the patient.

Example 12. The method according to any of examples 1-11, wherein the identifying a timing of a cerebral blood inflow and/or a cerebral blood outflow is based on identifying an R-wave of an ECG measurement of the patient.

Example 13. The method according to any of examples 1-12, further comprising draining a portion of a cerebrospinal fluid from the cerebral ventricle prior to the exchanging.

Example 14. The method according to any of examples 1-13, wherein the cerebral ventricle is a cerebral spinal fluid space.

Example 15. The method according to example 14, wherein the cerebral ventricle is found in a mechanical influence with at least a portion of an arterial vasculature of the patient.

Example 16. The method according to example 14, wherein the cerebral ventricle is found in a mechanical influence with at least a portion of a venous vasculature of the patient.

Example 17. The method according to example 16, wherein the venous vasculature is bridging veins of the patient.

Example 18. The method according to any of examples 1-17, wherein the flow of the cerebral blood inflow and/or cerebral blood outflow is enhanced by increasing cerebral blood volume in a range of 5-30%.

Example 19. The method according to any of examples 2-18, wherein the increasing intracranial pressure is in a range of 2-10%.

Example 20. The method according to any of examples 1-19, wherein the decreasing intracranial pressure is in a range of 2-20%.

Example 21. The method according to any of examples 1-20, further comprising discontinuing the shrinking when an intracranial pressure of the patient is detected as having a value below a predetermined threshold.

Example 22. The method according to any of examples 2-21, further comprising discontinuing the expanding when an intracranial pressure of the patient is detected as having a value above a predetermined threshold.

Example 23. A method for influencing cerebral perfusion in a patient by modifying a volume of a volume adaptor introduced into a cerebral ventricle of the patient, the method comprising: identifying a timing of a cerebral blood outflow in a cardiac activity of the patient; expanding a volume of the volume adaptor in synchronization to the identified timing of the cerebral blood outflow, to an amount sufficient to increase an intracranial pressure in the cerebral ventricle, such that a flow of the cerebral blood outflow is enhanced.

Example 24. The method according to example 23, further comprising identifying in the cardiac activity of the patient a timing of a cerebral blood inflow, and shrinking a volume of the volume adaptor in synchronization to the identified timing of the cerebral blood inflow, while decreasing intracranial pressure in the cerebral ventricle, such that a flow of the cerebral blood inflow is enhanced.

Example 25. The method according to example 23, wherein the expanding is provided in a rate of about 0.5 to about 1.5 ml/sec.

Example 26. The method according to any of examples 23-25, wherein the expanding is initiated prior to a prediction of the timing of a cerebral blood outflow.

Example 27. The method according to any of examples 24-26, wherein the shrinking is initiated prior to a prediction of the timing of a cerebral blood inflow.

Example 28. The method according to any of examples 23-27, further comprising detecting physiologic input of the patient and modifying a degree of the expanding according to the physiologic input.

Example 29. The method according to any of examples 24-28, further comprising detecting physiologic input of the patient and modifying a degree of the shrinking according to the physiologic input.

Example 30. The method according to any of examples 28-29, wherein the modifying the degree of the expanding and/or the degree of the shrinking occurs in a time interval of more than about 5 seconds.

Example 31. The method according to any of examples 28-29, wherein the modifying the degree of the expanding and/or the degree of the shrinking occurs in a time interval of more than about 1 minute.

Example 32. The method according to any of examples 28-31, wherein the detecting physiologic input comprises measuring a cerebral blood flow of the patient.

Example 33. The method according to any of examples 28-32, wherein the detecting physiologic input comprises measuring a cerebral perfusion pressure of the patient.

Example 34. The method according to any of examples 23-33, wherein the identifying a timing of a cerebral blood inflow and/or a cerebral blood outflow is based on identifying an R-wave of an ECG measurement of the patient.

Example 35. The method according to any of examples 23-34, further comprising draining a portion of a cerebrospinal fluid from the cerebral ventricle prior to the exchanging.

Example 36. The method according to any of examples 23-35, wherein the cerebral ventricle is a cerebral spinal fluid space.

Example 37. The method according to example 36, wherein the cerebral ventricle is found in a mechanical influence with at least a portion of an arterial vasculature of the patient.

Example 38. The method according to example 37, wherein the cerebral ventricle is found in a mechanical influence with at least a portion of a venous vasculature of the patient.

Example 39. The method according to example 37, wherein the venous vasculature is bridging veins of the patient.

Example 40. The method according to any of examples 23-39, wherein the flow of the cerebral blood inflow and/or cerebral blood outflow is enhanced by increasing cerebral blood volume in a range of 5-30%.

Example 41. The method according to any of examples 23-40, wherein the increasing intracranial pressure is in a range of 2-10%.

Example 42. The method according to any of examples 24-41, wherein the decreasing intracranial pressure is in a range of 2-20%.

Example 43. The method according to any of examples 24-42, further comprising discontinuing the shrinking when an intracranial pressure of the patient is detected as having a value below a predetermined threshold.

Example 44. The method according to any of examples 23-43, further comprising discontinuing the expanding when an intracranial pressure of the patient is detected as having a value above a predetermined threshold.

Example 45. A system for influencing cerebral perfusion in a cerebral ventricle of a patient, comprising: a volume adaptor having an expandable compartment sized and shaped to be introduced into the cerebral ventricle, the volume adaptor operable by switching between a shrunk state sized to decrease intracranial pressure and an expanded state sized to increase intracranial pressure; at least one sensor for measuring a physiologic output of the patient; and a processor in operating communication with the volume adaptor, and having instructions for predicting according to the physiologic input a timing of at least one of a cerebral blood inflow; and switching the volume adaptor into the shrunk state in synchronization with the timing of a cerebral inflow.

Example 46. The system according to example 45, wherein the processor further comprises instructions for predicting according to the physiologic input a timing of a cerebral blood outflow and switching the volume adaptor into the expanded state in synchronization with the timing of a cerebral outflow.

Example 47. The system according to example 46, wherein the synchronization is timed to be prior to the timing of a cerebral outflow.

Example 48. The system according to any of examples 45-47, wherein the synchronization is timed to be prior to the timing of a cerebral inflow.

Example 49. The system according to example 45, wherein the expandable compartment contains fluid.

Example 50. The system according to example 49, wherein the fluid comprises gas.

Example 51. The system according to example 49, wherein the fluid comprises liquid.

Example 52. The system according to any of examples 45-51, further comprising at least one pump being in fluid communication with the volume adaptor.

Example 53. The system according to example 52, further comprising a motor being in operative communication with the pump and the processor.

Example 54. The system according to any of examples 45-53, wherein the volume adaptor is provided in conjunction with an external ventricular drain.

Example 55. The system according to any of examples 45-54, further comprising a sensor for measuring cerebral blood flow.

Example 56. The system according to any of examples 45-55, further comprising a pressure sensor.

Example 57. The system according to any of examples 45-56, wherein the deformable compartment comprises a non-compliant wall.

Example 58. The system according to any of examples 45-57, wherein the deformable compartment comprises elastic walls.

Example 59. A method for influencing cerebral perfusion in a patient by modifying a volume of a volume adaptor introduced into a cerebral ventricle of the patient, the method comprising: identifying a timing of a cerebral blood inflow and/or outflow in a cardiac activity of the patient; modifying a volume of the volume adaptor in synchronization to the identified timing of the cerebral blood flow, to an amount sufficient to modify an intracranial pressure in the cerebral ventricle, such that a flow of the cerebral blood flow is enhanced.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-4G show exemplary simulations of volume changes of volume adaptor, and simulations of the intracranial blood pressure and the cerebral blood flow in a reference and after being affected by actively modifying cerebral fluid volume, in accordance with some embodiments of the invention, wherein FIG. 4A illustrates an example of an embodiment of a sequence of an adaptor volume change, FIG. 4B illustrates a second embodiment of a sequence, FIG. 4C illustrates a third embodiment of a sequence, FIG. 4D illustrates a simulation of intracranial pressure over time in a reference and when influenced by the method of the current invention, FIG. 4E simulates the ratio between the intracranial pressure of the reference and the current invention, as shown in FIG. 4D, FIG. 4F shows a simulation of the cerebral blood flow elevation over time in the current invention versus the cerebral blood flow in a reference without treatment, and FIG. 4G simulates intracranial pressure modification over time in an individual having high reference intracranial pressure;

FIGS. 5A-5B are block diagrams of optional systems for influencing cerebral perfusion pressure, in accordance with some embodiments of the invention, wherein FIG. 5A illustrates a general volume adaptor and FIG. 5B illustrates a specific embodiment of a volume adaptor in the form of a balloon;

FIGS. 7A-D illustrate various examples of a volume adaptor, in accordance with some embodiments of the invention, wherein FIG. 7A illustrates a deformable catheter, FIG. 7B illustrates a propelling catheter, FIG. 7C illustrates a double lumen catheter, and FIG. 7D illustrates a double catheter placed side by side;

DESCRIPTION OF SPECIFIC EMBODIMENTS OF THE INVENTION

Figure 1:
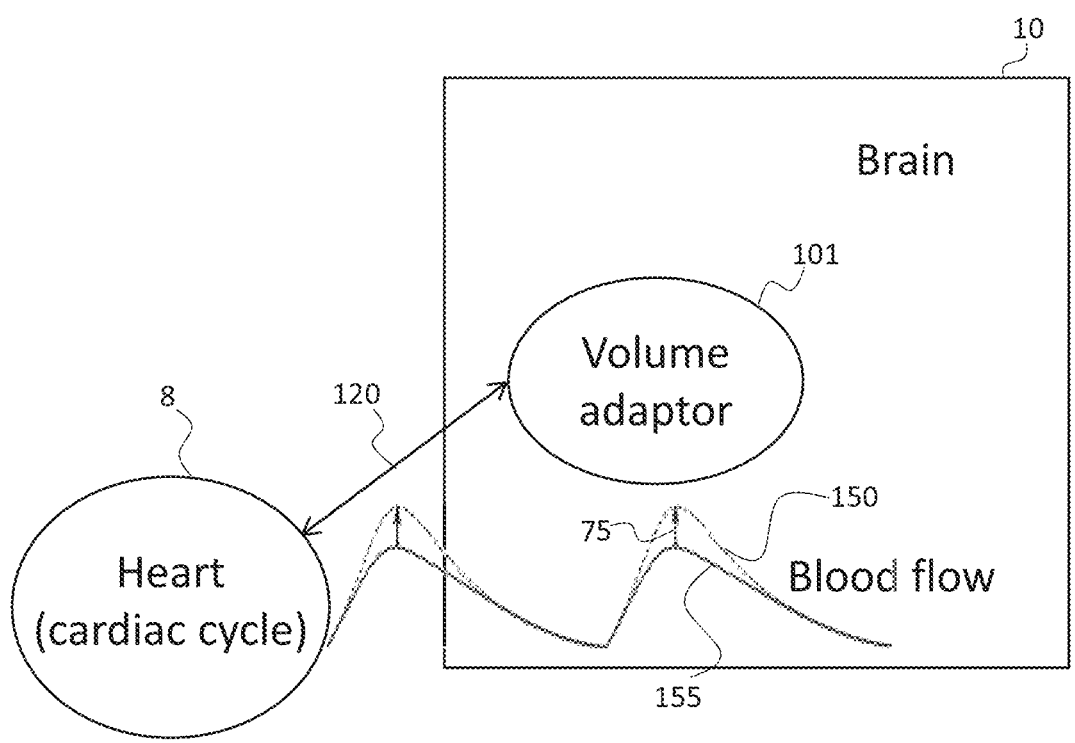
FIG. 1 is a block diagram showing a high level overview of the components interplaying in the system and method for actively influencing cerebral perfusion pressure in order to affect cerebral blood flow, in accordance with some embodiments of the current invention.

The present invention, in some embodiments thereof, relates to affecting cerebral blood perfusion and, more particularly, but not exclusively, affecting cerebral blood perfusion through intracranial pressure modification.

Overview

An aspect of some embodiments of the current invention relates to influencing cerebral blood flow by periodically changing intracerebral volume and/or pressure. In some embodiments, periodic alterations in intracerebral volume and/or pressure are synchronized to phases in the cardiac cycle. Optionally, timed modifications in intracerebral volume and/or pressure improve cerebral perfusion pressure and/or cerebral fluid flow. For example, fluid comprises blood and/or lymphatic fluid. In some embodiments, improvement in fluid flow is manifested in increased rate of flow and/or increased volume of inflow and/or increased volume of outflow. Optionally, the changes in volume use an expandable element, such as a balloon. In many embodiments herein the term balloon is used as an example, but can be understood to mean any expandable element, even if not a balloon.

In some exemplary embodiments of the invention, the alterations are between a state where the expandable element is in an expanded state and a state in which the expandable element is in a less expanded state (zero or some other baseline inflation). Optionally, change between states is rapid, for example, on the order of 10-20 ms.

In some exemplary embodiments of the invention, the alterations are timed so as to avoid a overall flattening of an ICP or CCP curve (e.g., alterations do not cause the peak and trough pressures to equalize or approximately equalize, though an individual peak or trough may be reduced in magnitude). Optionally, the alterations are timed so as to increase a volume during diastole. Optionally or alternatively, the alteration are timed so as to flatten or split a peak ICP. Optionally or alternatively, the alterations are timed to avoid increased volume of the expandable element during a systole. Optionally or alternatively, the alterations are timed so as to assist venous outflow during diastole.

The use of the terms diastole and systole relate to state of the arterial pulse in the brain, which is generally synchronized with the ICP (though generally preceding it by some ms). In the systole, the pressure increases and during diastole the pressure decreases, as a direct mechanical effect of the systole and diastole in the heart, but at a time delay relative thereto. It should be noted that systole in the heart (e.g., as indicated by an R-wave) is typically earlier than systole in the carotid arteries.

In some exemplary embodiments of the invention, the alterations are timed so as to provide a decreased expansion state of the expandable element during systole.

In some exemplary embodiments of the invention, the alterations are timed so that the expandable element is not maximally expanded during most of the cycle. For example, a duration of expansion of the expandable element by over 20% compared to a baseline expansion thereof is less than 80%, 60%, 30%, 20% or intermediate or smaller percentages of a cardiac cycle or ICP cycle.

In some exemplary embodiments of the invention, the alterations are timed so that expansion occurs a short time (e.g., between 10 and 400 ms, for example, between 30 and 200 ms or 50 and 150 ms) before de-expansion of the expandable element.

In some exemplary embodiments of the invention, the expansion rate is high, for example, expanding to a maximum volume in less than 80, 50, 20, 10 or intermediate number of milliseconds. Optionally, deflation is at a similar rate. Alternatively, deflation is allowed to be slower than expansion.

Typically, the brain is encased in a dura skull which serves as a fixed volume container. This may cause limited space in which brain tissue, cerebrospinal fluid and the blood circulating within the system can expand before intracranial pressure (ICP) rises. Probably due to the limited space, increased ICP may lead to reduced cerebral perfusion pressure (CPP), possibly by counteracting the arterial pressure within cerebral vessels. Reduced CPP may lead to decreased cerebral blood flow (CBF). Alternatively or additionally, increased ICP leads to reduced volume in vessels, which may also result in reduced blood volume due to the smaller available space, probably especially during the systolic phase which is characterized by blood inflow. Some clinical situations with increased ICP include, but are not limited to, head trauma and/or cerebral bleeding.

In some embodiments, cerebral fluid flow is enhanced by reducing the volume of the content residing in a cerebral ventricle, optionally in an active manner. For example, by introducing a volume adaptor, for example in the form of an expandable compartment, by shrinking the adaptor compartment, the volume which was taken up by the adaptor is freed, optionally allowing fluid in the cerebral ventricle to be spread over a larger volume, eventually causing a reduction in the fluid pressure in the cerebral ventricle. Potentially, reducing the intracranial pressure increases inflow of fluid into the cerebral region, possibly by not counteracting the vessels pressure and leading to an increase in CPP.

Alternatively or additionally, cerebral fluid flow is enhanced by increasing the volume of the content residing in a cerebral ventricle, optionally in an active manner. Typically, due to the limited space defined by the dura, an increase in cerebral content volume leads to an increase in the intracranial pressure. Potentially, ICP may help to squeeze cerebral fluid drainage, leading to increased cerebral fluid outflow.

Since reducing the cerebral volume may lead to increased cerebral fluid inflow, while increasing the cerebral volume may lead to increased cerebral fluid outflow, in some embodiments a tradeoff between improving the inflow and improving the outflow is resolved. In some embodiments, tradeoff between enhancing fluid inflow and enhancing fluid outflow is resolved by synchronizing volume decrease to at least a portion of the systole phase which is mostly characterized by fluid inflow, and/or by volume increase being synchronized to at least a portion of the diastole phase which is mostly characterized by fluid outflow. Alternatively or additionally, tradeoff is resolved by adapting the amplitude of the volume increase and/or decrease, for example by avoiding expanding the volume to an extent which would generate an ICP which may cease inflow. Alternatively or additionally, tradeoff is resolved by providing a gradual transition between a shrunk volume state and an expanded state, for example such as to reduce enough pressure to allow fluid inflow, while at the same time create enough pressure for squeezing fluid for increased outflow. In some embodiments, the tradeoff is resolved by synchronizing volume adaptation to the cardiac cycle, and choosing times to reduce the volume and/or times to increase the volume, in accordance with the expected blood flow compatible with the cardiac cycle phases.

In some embodiments, the trigger for increasing and/or reducing the cerebral volume is based on the cardiac cycle, optionally based on the ECG measurement. In some embodiments, a timing based on the R-wave of the ECG serves as the trigger for increasing and/or reducing the cerebral volume. In some embodiments, volume is actively varied when identifying an event in the timeline of a cardiac cycle, such as, for example, volume is reduced when determining the upcoming of a systolic pressure wave. In some embodiments, volume variation is conducted prior to an expected event, such as an expected change in inflow and/or outflow, to allow sufficient time for the variation to take place until the event occurs.

Optionally, direct measurement of the cardiac cycle is provided, for example by measuring an electrocardiogram (ECG), and/or measuring pulse, and/or measuring blood pressure. In some embodiments, cardiac measurements are conducted by a measuring probe, such as for example and electrode, positioned in proximity to the heart. Alternatively or additionally, measuring is conducted by measuring the pulse of the cerebral blood vessels, and/or by measuring the pulse and/or blood pressure in any region of the body. Optionally, phases of the cardiac cycle are calibrated to compensate for any delay between the measurement site and the volume adaptation site in the brain.

Optionally, determination of the onset of cardiac cycle phases is provided by extrapolation and/or prediction and/or machine learning. In some embodiments, the cardiac cycle is extracted from measurements of intracranial pressure and/or volume fluctuations.

Typically, performing volume modifications to a patient's brain is conducted while the patient is unconscious. It is therefore a potential advantage to monitor the effect of the volume modification by detecting and/or measuring physiologic input of the patient. In some embodiments, physiologic input is collected after each cardiac cycle. Alternatively or additionally, physiologic input is collected after more than two cardiac cycles. Alternatively or additionally, physiologic input is collected after more than five cardiac cycles. In some embodiments, physiologic input measurements determine the degree of increase and/or decrease of cerebral volume. Alternatively or additionally, physiologic input measurements determine the rate of the increase and/or decrease of cerebral volume.

In some embodiments, detection of physiologic input of the patient serves as a feedback. Optionally, these feedback measurements are used for tuning the degree of increasing and/or decreasing the cerebral volume. For example, measurements of physiologic input in the form of cerebral blood flow could indicate that the flow is too weak, and these measurements could be used for decreasing the cerebral volume, optionally, by increasing the shrinkage degree of a volume adaptor placed in the brain. In another example, measurements of physiologic input in the form of cerebral perfusion pressure could indicate that the CPP is too high. These measurements could be used for increasing the cerebral volume, optionally by increasing the expanding degree of a volume adaptor placed in the brain (which would lead to an increase in ICP, which would result in reduced CPP based on the calculation that CPP=MAP−ICP).

In some embodiments, one or more of the following indicators is used as part of or as a stand-alone treatment marker: tissue oxygenation, CBF, ICP, CPP values, integrals over time, smoothed values and/or time derivatives and/or morphology of their waveforms. Optionally, physiological markers correlated to any of these may be used, as well as other markers which indicate brain state and/or cerebral blood flow.

In some embodiments, physiologic input is collected at time intervals which are longer than a duration of a cardiac cycle. Therefore, in some embodiments, tuning of volume modification is provided at time intervals which are longer than a duration of a cardiac cycle. For example, modifying the degree and/or determining such need may occur in a time interval of once every about 5 seconds. In another example, modifying the degree may occur in a time interval of once every about 1 minute, or longer time periods, such as 5 minutes, 10 minutes, 20 minutes or intermediate or longer periods.

In some embodiments, CBF is improved by increasing cerebral volume during at least a portion of the diastole phase, possibly by retrograde flow which may lead to increased blood draining volume. In some embodiments, gradual increase of cerebral volume is performed. Potentially, gradual increase would allow a longer interval until the cerebral ventricle would go back to its pre-systolic conformation (expanded) and by that enable more time over the cardiac cycle where blood inflow can take place with less resistance owing to a more relaxed cranial vault. For example, small increments of volume increase in diastole, such as in the range of about 0.5 CC and about 2 CC, are configured to lead to a slight ICP elevation that would probably not affect arterioles, but potentially affect the venous system by leading to higher resistance to outflow. Optionally, it may be translated to elevated perfusion pressure within the brain tissue, potentially recruiting collateral circulation, and/or opening vessels in edematous tissue, and/or improving cerebral blood flow. The inventors have realized that increments in the range of about 0.1 CC to about 7 CC, for example, 0.5 to 5 cc, are capable to cause significant ICP changes in edematous brain, and potentially, changes within that range will probably suffice to exert venous congestion and recruitment of collapsed vessels upstream.

In some embodiments, a deflation over an inflation curve is used to identify forces that would potentially act on the delivery system and/or the drainage system. Optionally, reduced forces on the delivery system, such as the arterial system, create more space for fluid filling, potentially further promoting cerebral blood inflow. Also optionally, forces on the drainage system, such as the venous system, "squeeze" blood volume off the venous-end, potentially further promoting cerebral blood outflow.

In some embodiments, CPP is calculated as the difference between the mean arterial pressure (MAP) and ICP. In some embodiments, and currently used in improving CPP today, ICP reduction is provided, for example by hyperventilation, and/or hyperosmolar therapy, and/or CSF drainage, and/or heavy sedation. Alternatively or additionally, MAP augmentation is provided, for example by using amines to elevate systemic arterial pressure. A potential disadvantage of the above treatment options is exposing the patient to uncontrollable side effects of systemic treatment.

In some embodiments, CPP is modified by modifying the volume of the CSF fluid in a cerebral ventricle of a patient, such as by the use of an external ventricular device (EVD). Optionally, the volume of the CSF passively draining and/or returning through the EVD is augmented by actively changing the volume of the cerebral ventricle by a volume adaptor. In some embodiments, once the skull of a patient is penetrated and/or once a passive and/or active volume adaptor is inserted into a patient's cerebral compartment, some amount of the CSF outflows from the cerebral compartment. In such embodiments, when the volume of the volume adaptor is shrunk to a certain extent, the cerebral compartment contains a volume which is lower than a reference volume, i.e. the volume before penetrating the skull and/or inserting any device.

In an adult, CBF is typically 750 millilitres per minute or 15-20% of the cardiac output. In some embodiments, CPP is maintained at a pressure of about 50 to about 60 mmHg (or 60-160 mmHg), i.e. the mean arterial pressure (MAP) minus the ICP is at about 50 to about 60 mmHg. Typically, a decrease in CPP leads to a decrease in CBF. In some embodiments, if a patient has CPP level being lower, ICP is actively decreased in order to restore CBF to a substantially physiological level. An aspect of several embodiments of the invention relates to active cerebral volume variations synchronized to the cardiac cycle. In some embodiments, volume variation is provided by a volume adaptor locally inserted into a cerebral compartment of a patient, optionally a cerebral ventricle filled with CSF. In some embodiments, shrinking and/or expanding the adaptor causes changes in the volume of the cerebral compartment. In some embodiments, filling and/or draining the adaptor with fluid in the form of liquid causes changes in the volume of the cerebral compartment. Alternatively or additionally, filling and/or draining the adaptor with fluid in the form of gas causes changes in the pressure of the cerebral compartment. In some embodiments, reduction in the cerebral compartment volume and/or pressure by expanding the volume adaptor in the brain, at specific times of the cardiac cycle, leads to ICP reduction which, together with the flow stage of the cardiac cycle, enhances CPP and/or improves CBF. Alternatively or additionally, increase in the cerebral compartment volume and/or pressure by expanding the volume adaptor at other times of the cardiac cycle, leads to ICP increase which, together with the flow stage of the cardiac cycle, enhances CPP and/or improves CBF.

In some embodiments, a volume adaptor comprises a balloon. In some embodiments, when expanding the volume in the cerebral compartment the balloon is inflated with fluid, optionally gas. Alternatively or additionally, the balloon is inflated with liquid, optionally water and/or saline. In some embodiments, the balloon is deflated by pumping the fluid out of the confines of the balloon. In some embodiments, deflating the balloon comprises the use of temperature change, and/or acoustic transmission translated to balloon volume change, and/or electrical energy.

Optionally, a volume adaptor is provided in conjunction with an external ventricular drain device. In some embodiments, decreasing and/or increasing the cerebral volume in a brain ventricle containing CSF, provides a suction effect within the ventricles, optionally creating a force which enhances CSF flow to and from the brain ventricle.

In some embodiments, the balloon is filled with fluid from a reservoir. Optionally, the reservoir is located outside of the patient. Alternatively or additionally, the reservoir is provided inside the patient. In some embodiments, a balloon is actively filled with gas by a pump, and optionally the gas is passively drained to the ambient air by releasing a valve. Alternatively or additionally, at least two pumps are provided for optionally actively filling and actively draining the balloon. In some embodiments, a motor is provided to operate the at least one pump. Optionally, the motor is provided outside the patient. Alternatively or additionally, a motor is provided internally within the patient, optionally within the cerebral compartment, optionally within the adaptor device.

In some exemplary embodiments of the invention, a syringe pump is used. Optionally, the filling and/or emptying of the balloon is at a rate of at least 10 ml/sec, at least 50 ml/sec, at least 100 ml/sec, at least 250 ml/sec or faster or intermediate speeds. Optionally, the filling and/or emptying of a balloon occurs within between 1 and 50 ms, for example, between 5 and 30 ms, for example, about 10-20 ms. Optionally, faster speeds are provided so as to allow short inflation times. Optionally or alternatively, lower speeds are used to avoid jolting brain tissue.

Optionally, a volume adaptor comprises a non-compliant surface. Potentially, a non-compliant surface allows varying the pressure but not so much the volume of the volume adaptor. Alternatively, the volume adaptor comprises an elastic surface.

In some exemplary embodiments of the invention, the volume variations do not flatten the ICP as a whole.

In some exemplary embodiments of the invention, inflation is timed to not occur during times when the ICP is above a certain value. Optionally, the value is defined as a function of baseline ICP, peak ICP or value of ICP at certain parts of the cardiac cycle. Optionally, inflation is timed not to occur during systole. In some exemplary embodiments of the invention, inflation and deflation are applied even if ICP is between 30 and 50 mmHg.

In some exemplary embodiments of the invention, inflation is timed to occur just before deflation, so most of the cycle the balloon is not inflated beyond its baseline. Optionally, such inflation is used mainly to allow the deflation to have an effect on the brain. Optionally, inflation duration is optimized for that effect (e.g., long enough so deflation is effective but not much (e.g., <10% of cycle) longer).

An aspect of some embodiments of the invention relates to optimization of intracranial volume and/or pressure changes. In some exemplary embodiments of the invention, one or more of maximum (or minimum) volume (and/or pressure), volume (and/or pressure) change rate, volume (and/or pressure) change start, delay between inflation and deflation, duty cycle, inflation and/or deflation duration, volume change (and/or pressure) end, pressure and/or volume compliance and/or number of pulsations (inflation/deflation acts) per cycle are optimized per patient. Optionally, the optimization is changed over time, for example, in response to patient parameters.

In some exemplary embodiments of the invention, the optimization includes increasing a parameter until a desired mechanical and/or physiological effect is detected. Optionally, increase is stopped and/or reversed upon determination of an undesired effect and/or magnitude thereof, for example, mechanical and/or physiological.

An aspect of some embodiments of the invention relates to measuring and/or using a volume-pressure curve in a patient with a (suspected) cranial blood flow disorder. In some exemplary embodiments of the invention, the curve is estimated by injecting (e.g., inflating an intracranial balloon) with a known volume at a known time. Optionally, the known time is an end diastolic phase when the brain is as fluid drained as possible. Optionally, this time is determined by measuring ICP. At this time, a relationship between increase in volume and increase in pressure is determined. Optionally, the measurement is repeated over several cardiac cycles, optionally different amounts being injected at different ones of the cycles. Optionally, the injection volume is increased when the ICP stabilizes. In some exemplary embodiments of the invention, the injection is in steps of 0.1 cc and reaches up to a maximum of 5 cc. In some exemplary embodiments of the invention, the measurement is applied in addition, or instead, at other times of the cardiac cycle, for example, at maximum systole and/or at a time window covering times when injection for treatment is planned.

An aspect of some embodiments of the invention relates to controlling the expansion of an intracranial device in conjunction with fluid removal from the cranium. Optionally, fluid is removed before and/or simultaneously with expansion of the device, optionally under control of a single controller.

In some exemplary embodiments of the invention, fluid removal occurs during systole, while expansion of the device occurs during diastole.

In some exemplary embodiments of the invention, the device is maintained in at least a partially expanded state (e.g., between 0.1 and 0.7 cc, for example, about 0.5 cc) all through the cycle.

In some exemplary embodiments of the invention, the device is deflated back to a baseline state each systole and expanded (and the expansion possibly increased) during diastole.

In some exemplary embodiments of the invention, expansion increase is allowed only to an amount corresponding to fluid removal. For example, if fluid removal stalls, the maximum expansion volume is not increased.

An aspect of some embodiments of the invention relates to including more than one pulsation in at least some pressure cycles. It is noted that the pressure in the brain (ICP) varies over a cycle which is generally coordinated with the systemic blood pressure.

In some exemplary embodiments of the invention, deflation (volume decrease) is provided just before systole to allow more blood to enter the brain. Optionally, an additional pulsation is provided during diastole, for example, an inflation is used to collapse veins and reduce intracranial fluids. Optionally, such inflation is followed by deflation, so as to allow increased arteriole flow.

In some exemplary embodiments of the invention, the amplitude of the two pulsations is different, for example, a lower amplitude is provided for the additional pulsation. Optionally or alternatively, the shapes of the two pulsations is different. Optionally, further additional pulsations (e.g., 1, 2, 3, or more) are provided during the cycle, for example, during diastole and/or during systole, optionally with a volume which does not increase ICP (or CCP or other pressure measure) over a peak value provided by the first pulsation. Optionally, the number and/or timing of such pulsations is determined using a search and/or optimization procedure and/or is subject to change due to device adjustment, for example, as described herein.

It is noted that in some embodiments, a pre-systolic pulsation is not provided, with only a single (e.g., diastolic pulsation) or additional pulsations provided.

A broad aspect of some embodiments of the invention relates to synchronizing changes in fluid volume in the brain to cranial pressure cycles. In one example, fluid is removed or injected at a known, and optionally repeatable time in the cycle. This may be used to generate a pressure-volume curve. In another example, fluid injection and/or removal is timed to match expansion and/or deflation of an expandable intra-cranial element, optionally resulting in a substantially zero total change in volume (artificial input~artificial output) over a cycle or over a smaller part of a cycle (e.g., 500 ms).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

High Level Overview

Referring now to the drawings, FIG. 1 shows a high level overview of the components interplaying in the system and method for actively influencing cerebral perfusion pressure in order to affect cerebral blood flow, in accordance with some embodiments of the current invention.

In some embodiments, a volume adaptor 101 is introduced into a brain 10 of a patient, optionally into a cerebral spinal fluid (CSF) space, e.g. a cerebral ventricle having CSF, a sub-dural location or a spinal location. In some embodiments, volume adaptor 101 is configured to actively enhance and/or decrease its volume. Optionally, by being surrounded in a deformable environment, such as by CSF, the volume changes of volume adaptor 101 affect the extent the deformable environment is pushed against its confinements, i.e. the changes in volume of adaptor 101 affect the pressure exerted by the cerebral ventricle, potentially affecting the intracranial pressure in a global manner.

Influencing the intracranial pressure, in accordance with timing of phases of the cardiac cycle, in some embodiments, leads to increased cerebral perfusion pressure (CPP), optionally also leading a changed cerebral blood flow 150 which is enhanced from a reference cerebral flow 155 by a percentage 75. In some embodiments, enhancement of cerebral flow comprises larger volumes of blood flowing in and/or flowing out. Alternatively or additionally, enhancement comprises increasing the flow rate.

In some embodiments, an activity of heart 8 is detected. Optionally, the activity is detected by electrodes providing an electrocardiogram. Alternatively or additionally, an activity is detected by pulse measurement (e.g., in or on an artery such as the carotid) and/or blood pressure, optionally cerebral blood pressure. In some embodiments, a cardiac cycle waveform is extracted from measurements of the heart 8 activity. Alternatively or additionally, a cardiac cycle waveform is derived by extrapolation of other measurements, such as intracranial pressure variations. In some embodiments, a cardiac cycle waveform is anticipated by machine learning before its onset. In some embodiments, a cardiac cycle waveform comprises identifying at least one event, which is either a systolic phase or a diastolic phase. In some embodiments, identifying comprises determining an inception of a phase. Alternatively or additionally, identifying comprises predicting an inception. Alternatively or additionally, identifying comprises determining and/or predicting a peak of a systolic and/or diastolic wave.

In some embodiments, the activity of heart 8 influences 120 the timing and/or directionality the volume change of adaptor 101. Optionally, a timing and/or direction of a volume change of volume adaptor 101 and reservoir are synchronized with the cardiac activity of heart 8. For example, when a systolic power wave is determined, the volume adaptor 101 may be shrunk, in order to potentially decrease ICP and thus allow more blood volume to fill in the cerebral compartment found in brain 10. In some embodiments, volume adaptor 101 is expanded, in order to increase the volume, and therefore potentially the pressure, residing inside the cerebral compartment, possibly aiding to squeeze blood, for example during at least a portion of a diastolic wave. Optionally, during a crest period between a systolic wave and a diastolic wave, the volume of the adaptor 101 is maintained. Additional exemplary timing options are described hereinabove and below.

Figure 14A:
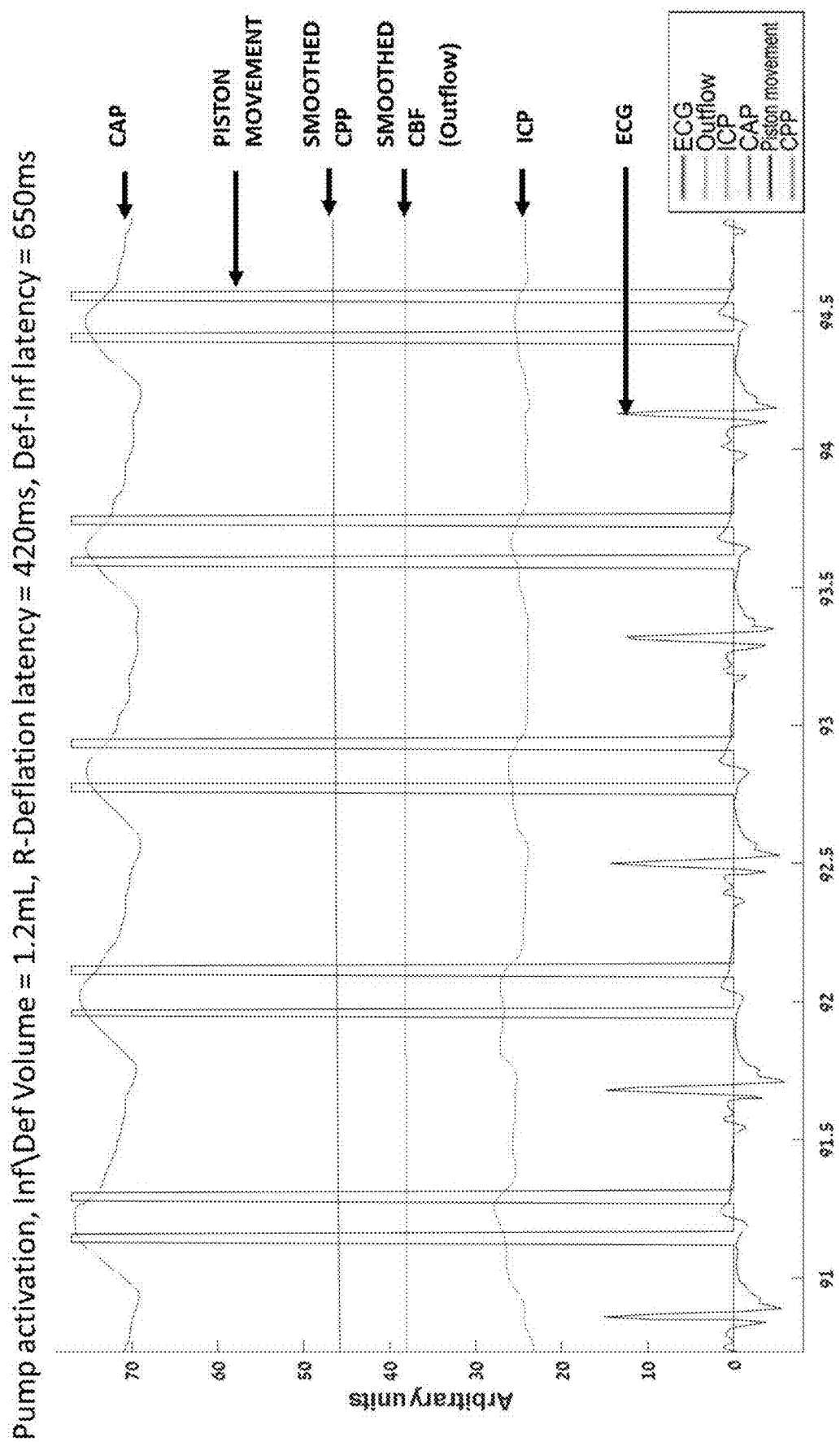
FIGS. 14A (detail view) and 14B (general view) illustrate degradation in brain condition when using incorrect timing applied to some embodiments of the invention.
Figure 14B:
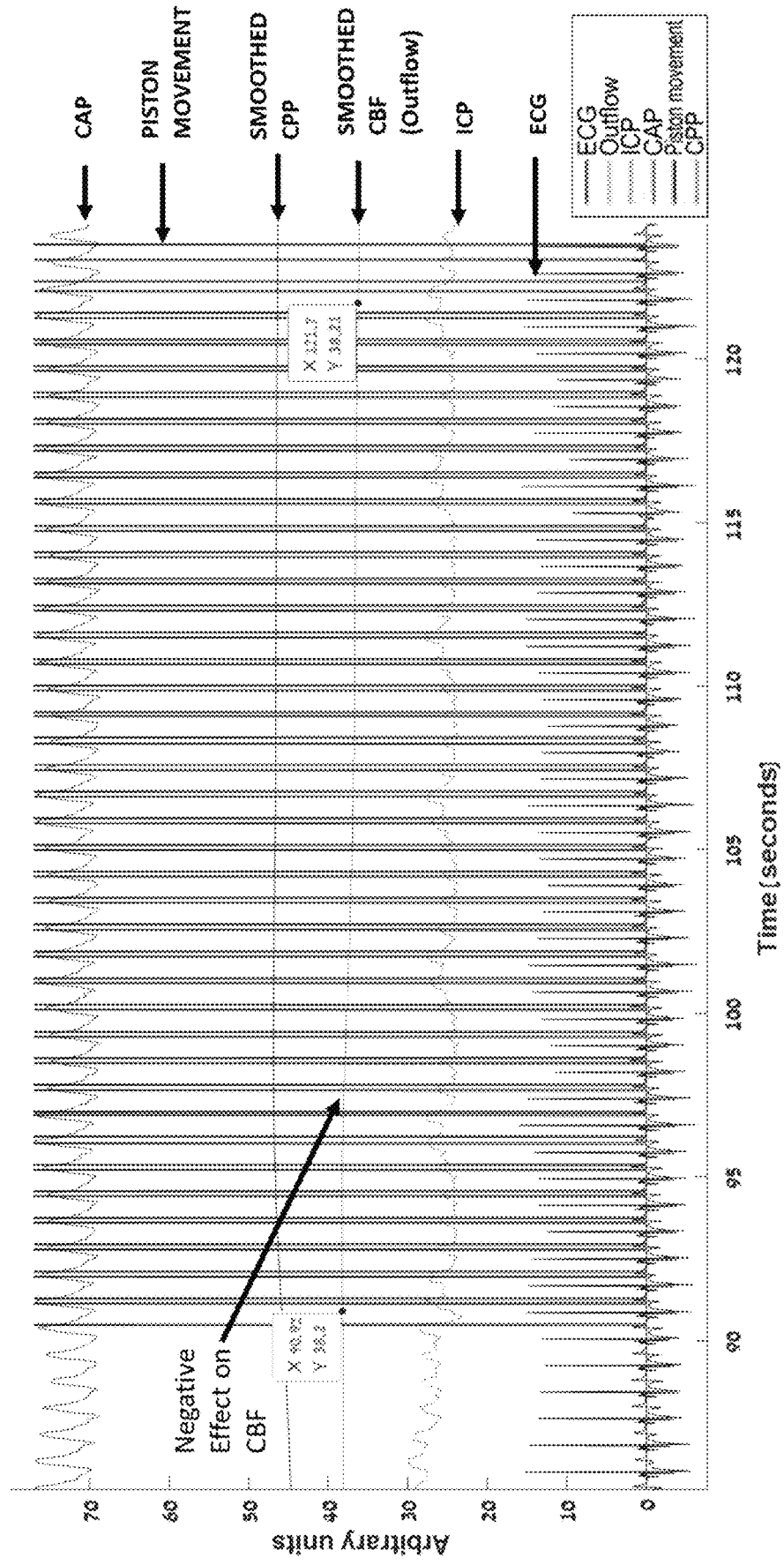

A potential advantage of synchronizing timing and amplitude (i.e. amount of volume) of the change in volume between adaptor 101 and the cardiac activity, is to settle a tradeoff between increasing too much intracranial pressure and eliminating blood inflow to decreasing too much intracranial pressure and eliminating blood outflow. By synchronizing to the cardiac cycle, the flow waveform of the blood is potentially used to increase and decrease the intracranial pressure such that in at least a portion of the time blood flow is enhanced. In some embodiments, changing the proportion between increasing and decreasing timing and amplitude varies the portion of time and the quality of flow enhancement 75. For example, FIGS. 14A and 14B illustrate an example of timing which does not have a beneficial effect on flow enhancement.

In some embodiments, flow enhancement 75 comprises an increase in cerebral blood volume, for example, an increase of about 0.5 ml to about 2 ml, and/or an increase of about 1 ml to about 3 ml, and/or an increase of about 3 ml to about 5 ml. Alternatively or additionally, flow enhancement 75 comprises an increase in cerebral blood flow rate, for example, an increase to about 14-16 cm/s in the arteries and/or veins, and/or to about 0.02-0.04 cm/s in the capillaries. In some exemplary embodiments of the invention, parameters of the treatment are varied in order to reach one or more of the above increase or other changes in physiological parameter values. Some exemplary methods are described below.

Some Exemplary Possible System Outcomes and Behaviors

Figure 2:
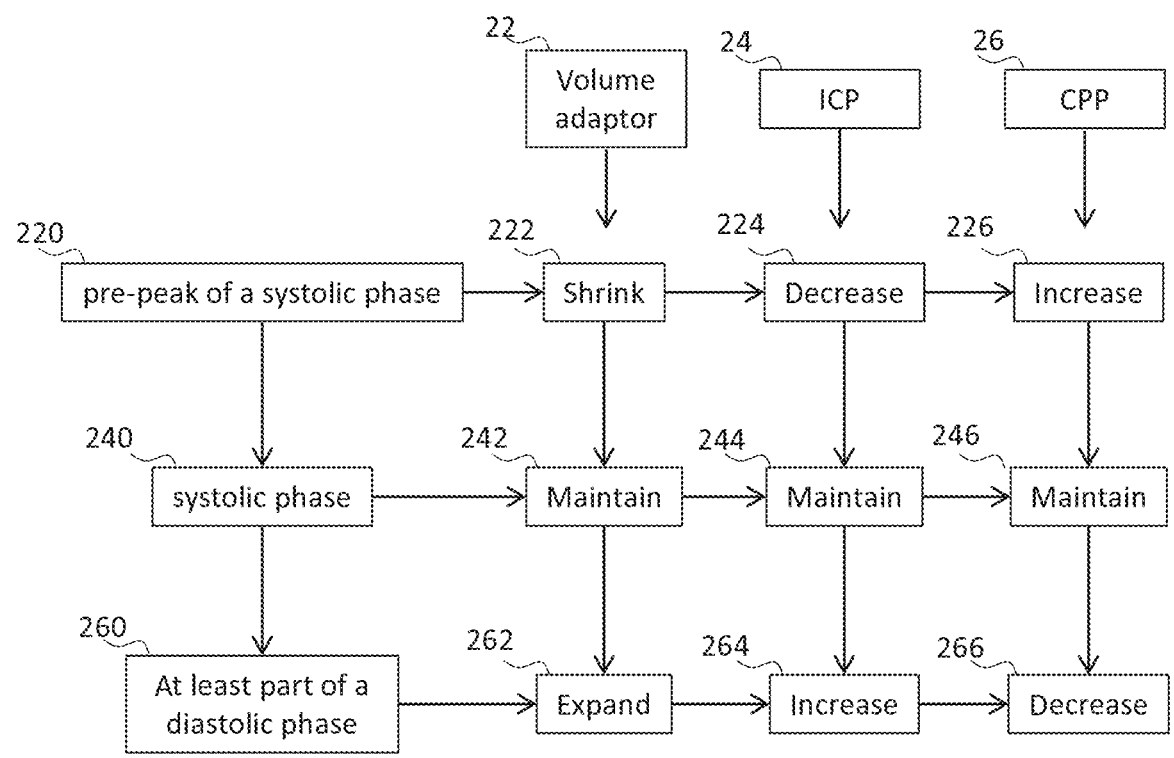
FIG. 2 is a flowchart illustrating possible outcomes of a volume of a volume adaptor, an intracranial pressure and cerebral perfusion pressure when synchronized to the cardiac cycle, in accordance with some embodiments of the current invention.

Reference is now made to FIG. 2, showing a flowchart illustrating possible outcomes of a volume variation of a volume adaptor, an intracranial pressure variation and cerebral perfusion pressure variation when synchronized to the cardiac cycle, in accordance with some embodiments of the current invention.

In some embodiments, a volume of an adaptor 22 is shrunk 222 when identifying a pre-peak of a systolic phase, i.e. when predicting that the height of amplitude of a systolic pressure wave is approaching 220. In some embodiments, when volume is shrunk in 222, the ICP 24 decreases 224. A decreased ICP 24 in 224 when timed with a systolic pressure wave approaching 220 potentially results in less CPP 26 and also more volume to allow inflow of blood to fill cerebral delivery systems, such as arterial and/or arteriolar systems.

In some embodiments, the decreased volume 222 is maintained throughout at least a portion of the systolic phase 240, and optionally during its entire duration. In some embodiments, while volume is maintained at 242, pressure is maintained in 244 and 246 indicating ICP 24 and CPP 26 respectively. In some embodiments, CPP might be elevated due to increased blood inflow during the systolic phase.

In some embodiments, during at least a portion of the diastolic phase 260, volume adaptor 22 is expanded 262. Optionally, this leads to an elevation 264 in ICP 24, and as a result of that to decreased 266 of CPP 26, possibly leading to reduced overload over a drainage system, such as a cerebral venous system, which potentially results in increased blood outflow. Optionally, the cerebral venous system is the bridging veins.

Exemplary Method for Influencing Cerebral Perfusion Pressure

Figure 3:
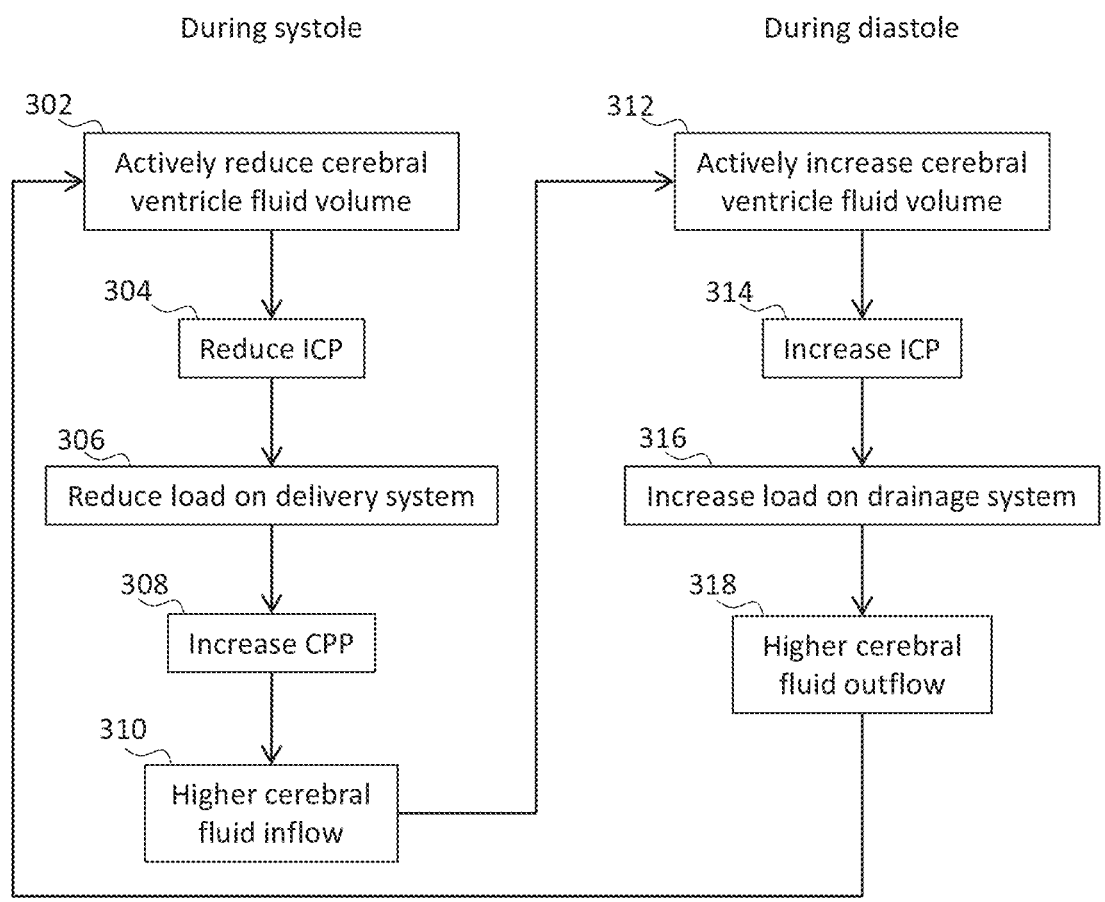
FIG. 3 is a flowchart illustrating a method for influencing cerebral perfusion pressure, in accordance with some embodiments of the current invention.

Reference is now made to FIG. 3, showing a flowchart illustrating a method for influencing cerebral perfusion pressure, in accordance with some embodiments of the current invention.

In some embodiments, cerebral ventricle fluid volume is actively shrunk 302 by means of a volume adaptor introduced into a cerebral compartment of a patient. Optionally, the volume is shrunk 302 below a reference volume because during the insertion of the volume adaptor, some CSF is drained from the cerebral compartment, leading to a new lower reference volume. Typically, reduced ventricle fluid volume results in less fluid volume in the relatively fixed volume compartment of the brain which leads to reduced intracranial pressure 304. Optionally, reduced ICP leads to reduced load on a delivery system 306, which leads to increased cerebral perfusion pressure 308. In some embodiments, increased cerebral perfusion pressure in 308 allows more fluid, such as blood and/or lymphatic fluid, to flow into the cerebral compartment. Optionally, when 302-310 is provided in synchronization with the systolic phase of the cardiac cycle, which is characterized mostly by high inflow, the effects of 302-308 over 310 are enhanced.

In some exemplary embodiments of the invention, shrinking 302 is performed so that the adaptor is at its baseline volume before systole starts. In some embodiments, shrinking continues after systole starts, for example, there being an overlap of between 2% and 20% or more of the systole with a partially expanded adaptor. It is noted that the baseline state of the adaptor may have a volume larger than zero, for example, to ensure some minimal volume to work with if ICP increases or the ventricles collapse.

In some embodiments, when systolic phase is over or alternatively, when predicting (e.g., based on R-R interval length and/or shape of pulse wave and/or previous cycles) that it will be over shortly (e.g., in a time range of 0.05-0.2 sec prior to the systolic phase ending), a cerebral ventricle is actively filled with fluid volume 312. Typically, increasing the volume in the fixed volume of the brain compartment leads to ICP increase 314, which in turn may increase the load on a drainage system, such as a venous system. In some embodiments, the increased load acts as a squeezer which assists cerebral fluid outflow. Optionally, when 312-318 is provided in synchronization with the diastolic phase of the cardiac cycle, which is characterized mostly by high outflow, the effects of 312-316 over 318 are enhanced. In some embodiments, filling is provided closer to the beginning of the systolic phase, as a preparatory step for fluid removal during and/or just before systole.

Exemplary Simulation of the Effects of Modifying Intracranial Pressure

Reference is now made to FIGS. 4A-G, showing exemplary simulations of the intracranial blood pressure and the cerebral blood flow in a reference and after being affected by actively modifying cerebral fluid volume, in accordance with some embodiments of the invention.

Figure 4A:
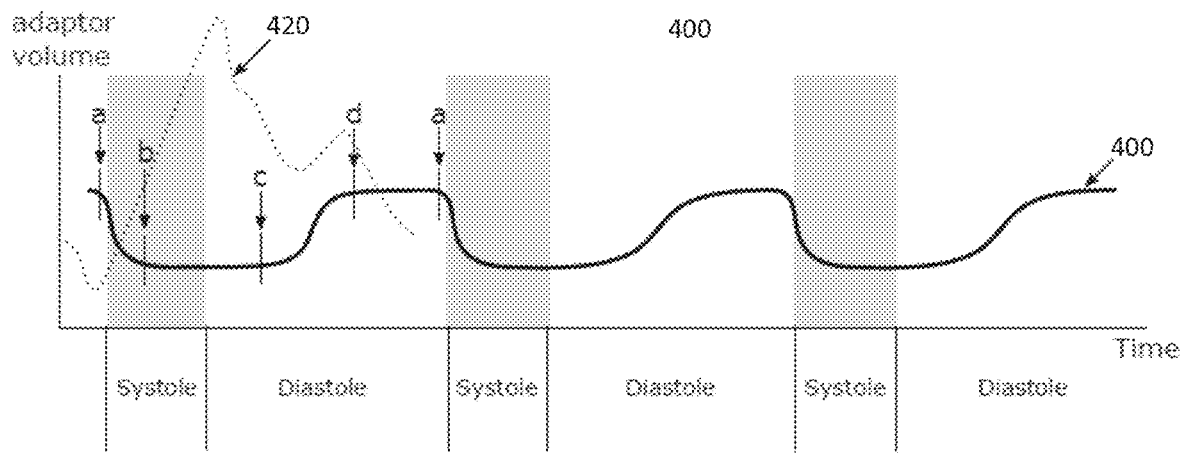
Figure 4B:
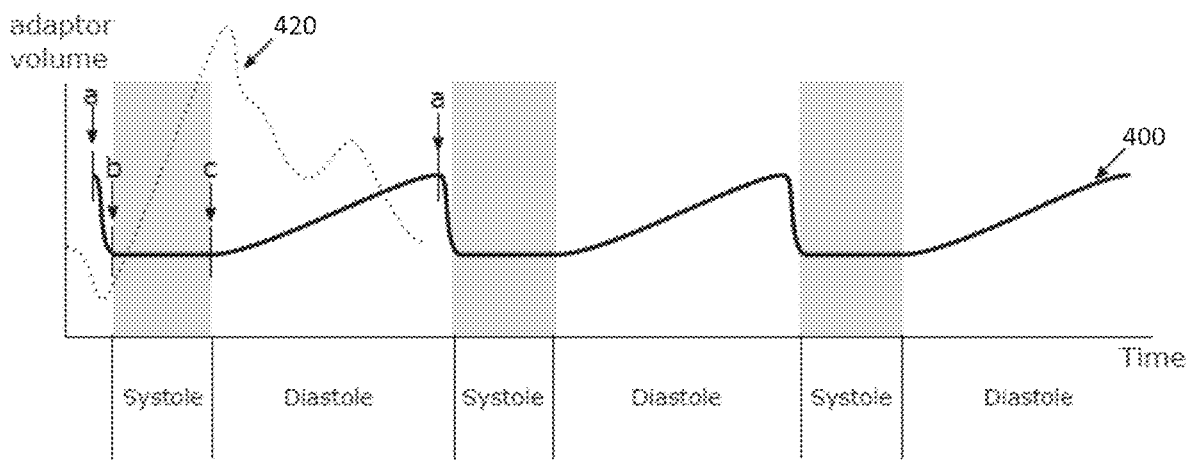
Figure 4C:
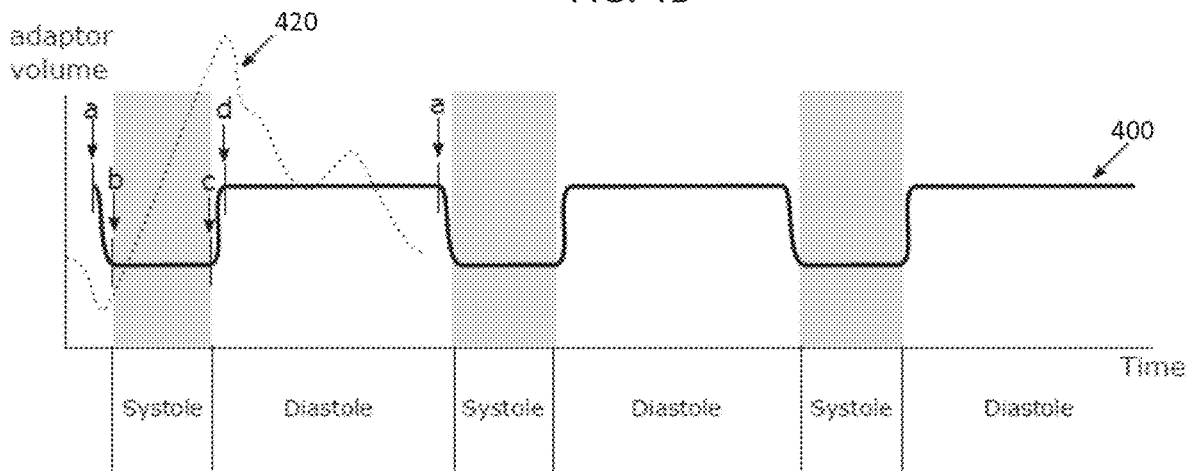

FIGS. 4A-4C illustrate examples of sequences 400 of changing an adaptor's volume. In some embodiments, sequence 400 is synchronized to at least a portion of a cardiac cycle 420. In some embodiments, sequence 400 is iterative and repeats the same pattern in each cardiac cycle. Alternatively, sequence 400 is altered between cycles, optionally following measured physiologic input from the patient. In some embodiments, physiologic input is a cardiac activity, such as cycle phases and/or pulse and/or blood pressure. Alternatively or additionally, physiologic input is related to brain measurements, and includes ICP and/or CPP and/or CBV and/or CBF rate.

In some embodiments, the specific profile of sequence 400 is determined based on the specific pathology of the patient. For example, a patient having low compliance could be treated by relatively fast and small transitions of volume adaptation (e.g., with speed and volume selected according to the available compliance). Optionally, the specific profile is modified in real-time based on physiologic input collected during the volume adaptation and affecting subsequent cycles of adaptation.

Optionally, adaptor volume is synchronized with cerebral blood inflow and/or outflow. In some embodiments, cerebral blood flow is measured directly by a flow sensor. Alternatively or additionally, cerebral blood flow is inferred from other brain and/or heart related physiologic input.

Reference is now made to FIG. 4A. In some embodiments, decrease in the volume of the volume adaptor is synchronized with cerebral blood inflow, such as shown in section a-b, optionally beginning in point a at the beginning of the systolic phase. In some embodiments, point a is synched to a time after the inception of the systolic phase. Optionally, volume adaptor is maintained in a shrunk state, such as shown in plateau b-c, starting at point b which is optionally a time before a peak pressure of the systolic pressure wave, and ending in point c. In some embodiments, point c leads to an expanding period, such as shown in section c-d. Optionally, point c is timed at a time point during the diastole phase. Alternatively, point c starts before inception of diastole to already allow squeezing of cerebral blood outflow. In some embodiments, expansion c-d is gradual, e.g. in a range of about 0.5-1.5 ml/sec, optionally resulting in a total expansion in a range of about 0.5 ml-3.5 ml. Alternatively, rise in expansion c-d is steep. In some embodiments, following an expansion c-d, a plateau in the expanded state is maintained, such as shown in section d-a.

Reference is now made to FIG. 4B, illustrating an example wherein the plateau of b-c ends at the systolic phase end in point c, and followed by a gradual increase in volume c-a, without a plateau, and beginning again in point a in a decrease in volume prior to the systolic phase.

Reference is now made to FIG. 4C, illustrating an example wherein the changes in volume, such as decrease a-b and increase c-d, are steep, and in between the changes, plateaus b-c and d-a are maintained, optionally substantially along the entire length of the remainder of the cardiac phase.

In some embodiments, point c, which in FIGS. 4A-4C stands for the transition from a shrunk state to an expanded state, is determined such that a tradeoff is settled between allowing the inflow of the systole and enabling the outflow of the diastole. For example, the tradeoff is resolved by selecting a point in time before the end of the systole and/or before the start of the diastole, to allow enough pressure to increase to allow the outflow, but still allow the inflow of the end of the systolic phase. Alternatively, for example, volume decrease, such as in point a, begins before the start of the systolic phase and/or the end of diastolic phase, to prepare the decrease in pressure for the inflow characterized in the systole.

In some embodiments, plateaus are determined in sections which are characterized by a dominant flow pattern, i.e. either substantially exclusive inflow or either substantially exclusive outflow. Other shapes maybe provided, such as including one or more troughs and/or peaks in the plateau, optionally the plateau being a series of pulsations, optionally with a volume amplitude of less than 50% of a pre-systolic pulsation.

Figure 4D:
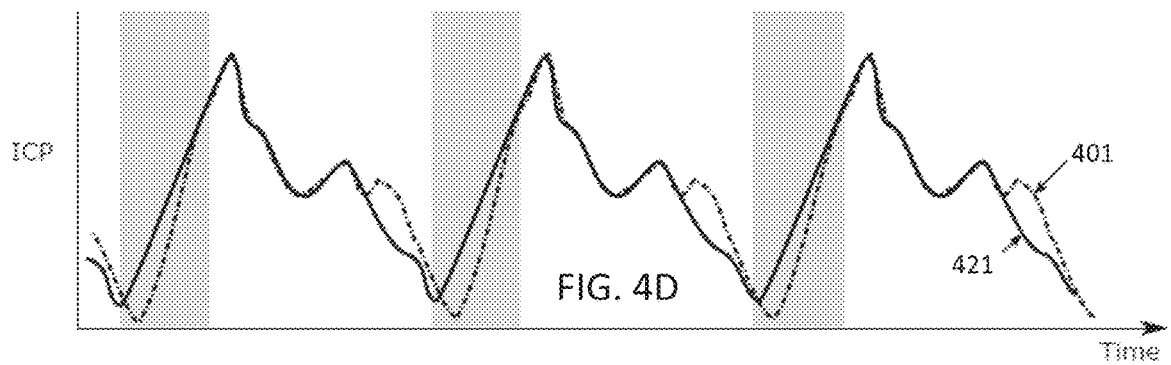

FIG. 4D illustrates a simulation of intracranial pressure over time in a reference 421 and when influenced 401 by volume adaptation, in accordance with some embodiments of the present invention. Shown is an example for a decrease in ICP following volume reduction in the adaptor, and an increase in ICP following an increase in the volume of the adaptor.

Figure 13A:
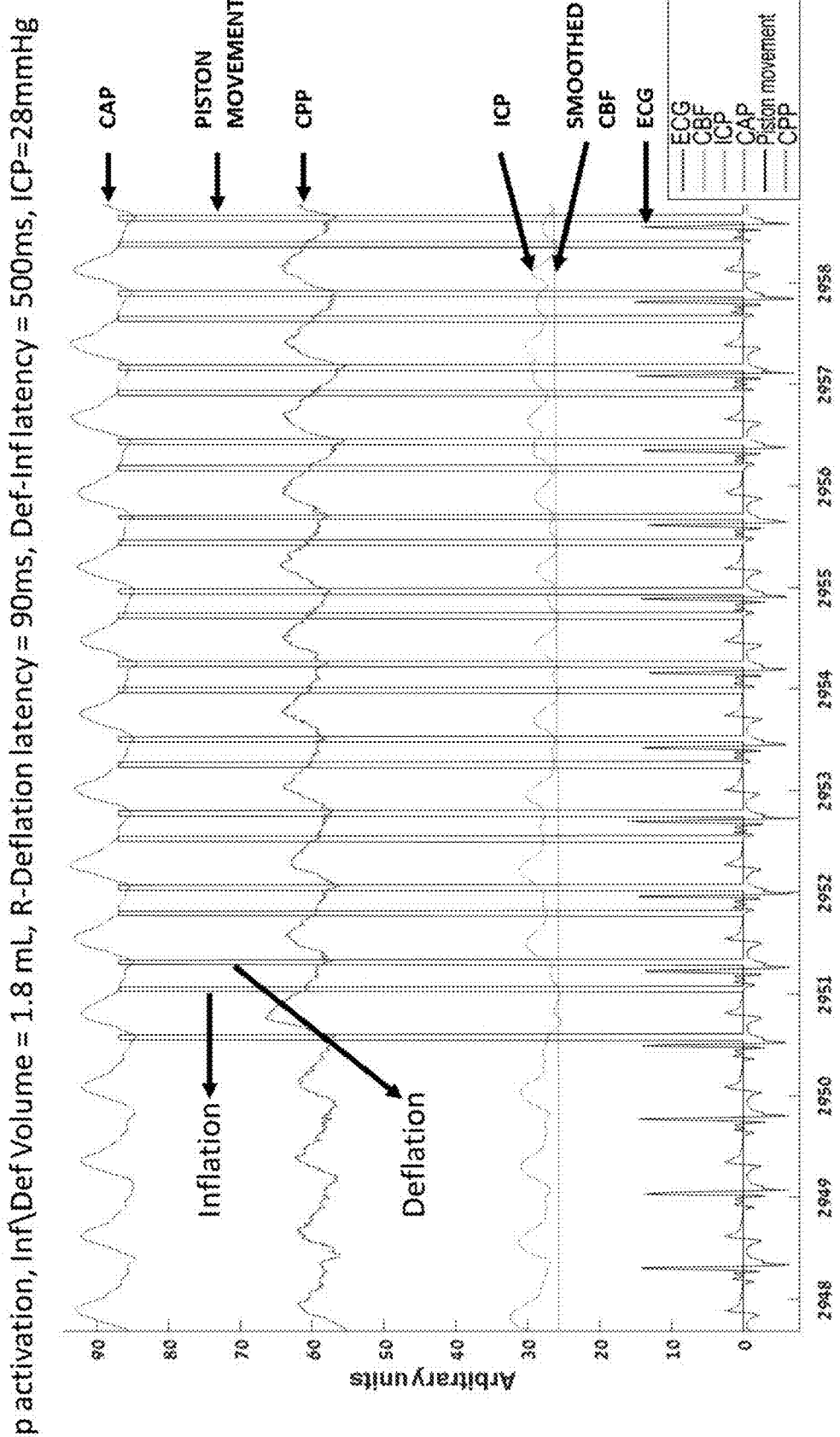
FIGS. 13A and 13B illustrate improvements in brain condition when using correct timing, in accordance with some embodiments of the invention.
Figure 13B:
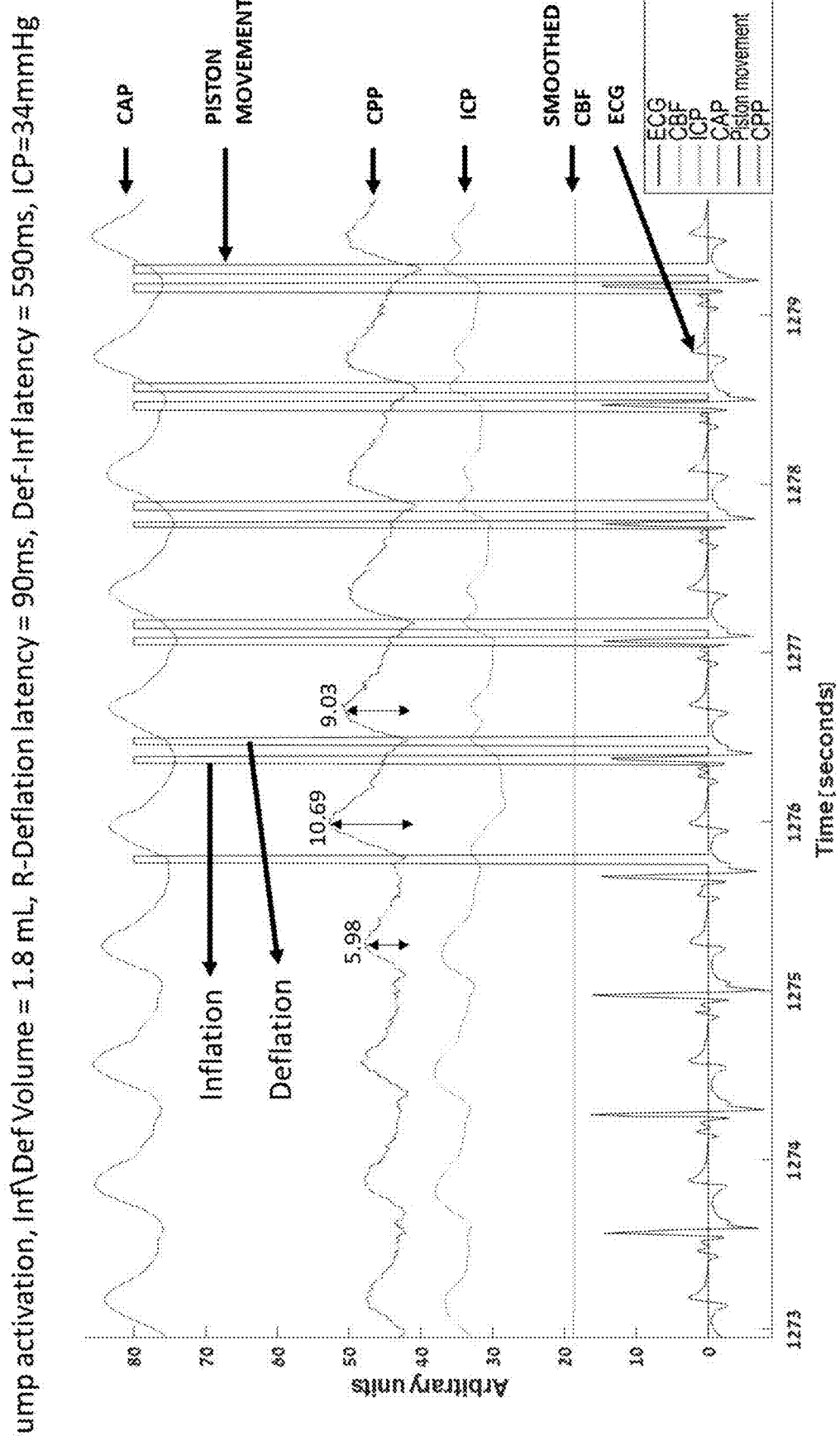

FIGS. 13A and 13B show one potential desired effect of volume modification, in that a peak pressure is reduced in maximum amplitude and/or split (into two or more smaller peaks) and/or flattened (having a less acute angle).

Figure 4E:
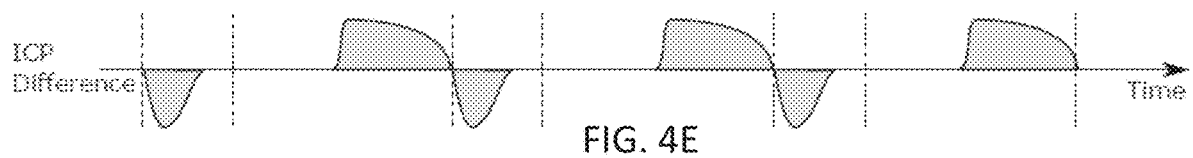

FIG. 4E simulates the ratio between the intracranial pressure of the reference 421 and changed trend line 401, as shown in FIG. 4D. It is noted that while ICP increased during diastole, it optionally does not reach the peak value found in systole.

Figure 4F:
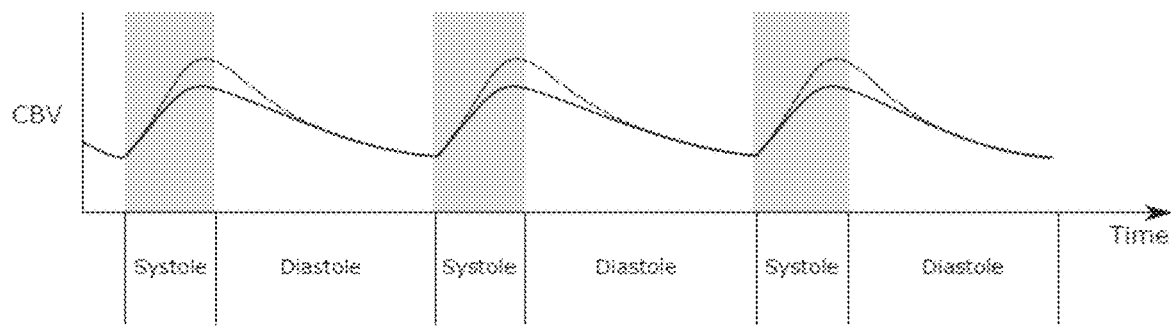

FIG. 4F shows a simulation of the cerebral blood flow elevation over time in accordance with some embodiments of the current invention versus the cerebral blood flow in a reference without treatment. Shown is exemplary elevation of blood inflow found in the peak of the systolic pressure wave.

Figure 4G:
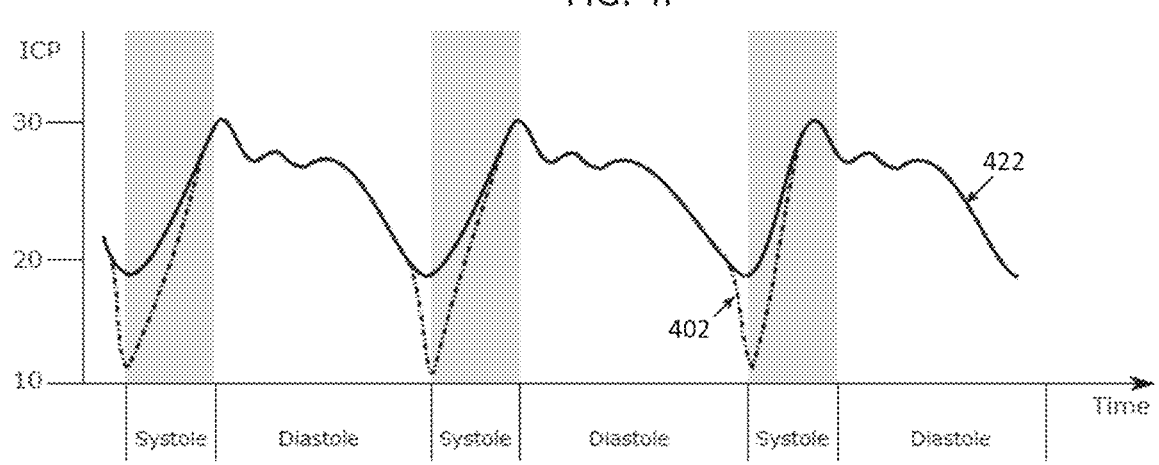

FIG. 4G simulates intracranial pressure modification 402 over time in an individual having high reference intracranial pressure 422. In some embodiments, as in the shown example, the pressure is only reduced below the reference and is not elevated above the reference. Typically, in cases of high reference intracranial pressure, the influence of reducing the ICP is more prominent.

Exemplary System for Influencing Cerebral Perfusion Pressure

Figure 5A:
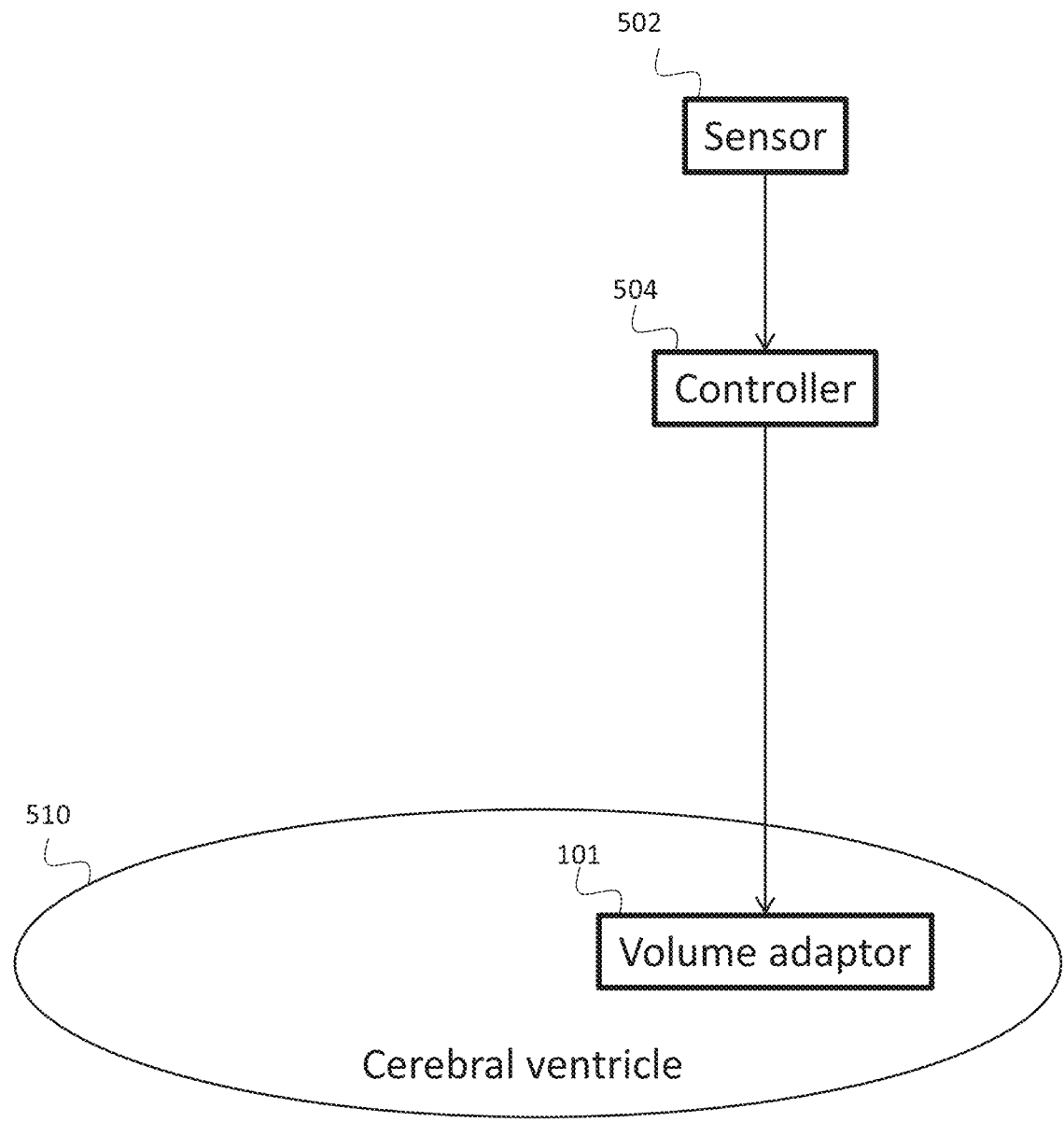
Figure 5B:
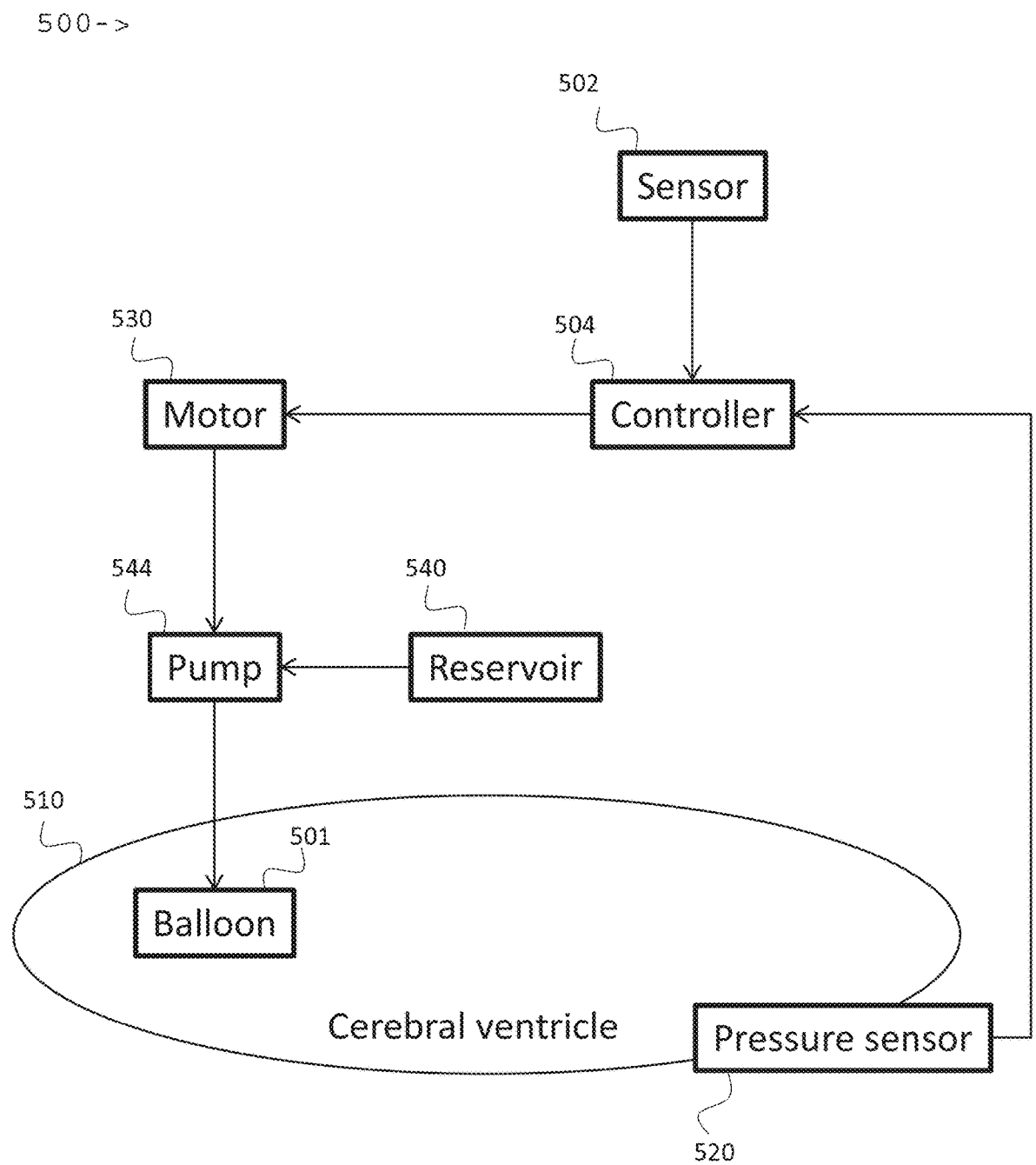

Reference is now made to FIGS. 5A-B, showing block diagrams of optional systems for influencing cerebral perfusion pressure, in accordance with some embodiments of the invention, wherein FIG. 5A illustrates a general volume adaptor and FIG. 5B illustrates a specific embodiment of a volume adaptor system 500 using an expander (101) in the form of a balloon.

In some embodiments, a system includes a volume adaptor 101 residing in a cerebral ventricle 510 of a patient. In some embodiments, volume adaptor 101 influences the intracranial pressure of the patient by modifying the content volume inside the cerebral ventricle. In some embodiments, controller 504 is found in operable communication with volume adaptor 101. For example, controller 504 has instructions which result in the shrinking of adaptor 101. Alternatively or additionally, controller 504 has instructions which result in the expanding of adaptor 101. Optionally, controller 504 communicates with a motor residing within adaptor 101. Alternatively or additionally, controller 504 communicates with an external motor 530, as shown in FIG. 5B.

In some embodiments, controller 504 receives input from at least one sensor 502. For example, sensor 502 can detect cardiac activity, such as cardiac electricity and/or pulse and/or blood pressure. Alternatively or additionally, sensor 502 can detect intracranial pressure and/or cerebral perfusion pressure and/or cerebral blood flow rate and/or cerebral blood volume (e.g., as indicated with a cerebral sensor 520, for example, an intra-cranial sensor, for example, an intracranial pressure sensor).

In some embodiments, controller 504 comprises instructions for identifying in the cardiac activity timings of cerebral blood inflow, such as approximately around the time of the systole phase, and/or timings of cerebral blood outflow, such as approximately around the time of the diastole phase. Optionally, controller 504 operates adaptor 101 to shrink in synchronization to timings of cerebral blood inflow. Alternatively or additionally, controller 504 operates adaptor 101 to expand in synchronization to timings of cerebral blood outflow.

In some embodiments, controller 504 further comprises instructions for predicting the timings of inflow and/or outflow. Optionally, synchronization is timed to precede its change in operation to an expected change in flow. For example, adaptor 101 may be shrunk prior to or after a predicted inception of an inflow. A potential advantage of synchronization which includes a temporal offset to the inflow and/or outflow and/or other physiological events is maintaining the tradeoff between the contradicting influence of pressure over inflow and outflow, perfusion and/or affecting various regulatory cycles.

In some embodiments, at least one more sensor is provided, such as for example a CBF monitor, and/or PbtO2 monitor, and/or CPP(t) and/or CPP integral (e.g., an integral over time) and/or ICP(t) and/or ICP integral (ICP/CPP dose). Optionally, measurements from at least one of these sensors is used for determining the amplitude of shrinking and/or expansion of the device. In some exemplary embodiments of the invention, the integral is over a period of between 1 and 600 seconds, for example, between 5 and 10 seconds.

In some embodiments, a pressure sensor (e.g., 520) in provided for measuring the pressure in at least two distinct points of a cerebral vessel of the patient. Alternatively or additionally, at least one flow sensor is provided. Optionally, operation of said volume adaptor is discontinued when in the vessel an undesired pressure difference and/or the absence and/or otherwise undesirable amount of a fluid flow are detected between the two distinct points.

Optionally, controller 504 comprises instructions to cease expanding volume adaptor 101 when the pressure sensor provides a value which is above a predetermined threshold, for example, above 15 mmHg, or above 20 mmHg, or above 25 mmHg, or above 30 mmHg, or above 35 mmHg.

Optionally, controller 504 comprises instructions to cease shrinking volume adaptor 101 when the pressure sensor provides a value which is below a predetermined threshold, for example, below 5 mmHg, or below 4 mmHg, or below 3 mmHg.

In some exemplary embodiments of the invention, controller 504 includes instructions to perform searching for initial values and/or adapting values of system parameters.

In some exemplary embodiments of the invention, controller 504 includes instructions for calculating a PV curve.

In general, it is noted that all methods described herein specifically, sensing, analyzing sensed signals, inflating and deflating and deciding on and/or actually changing system parameters (other than, possibly, physically inserting expander 101 into the skull), may be performed under control and/or notification of controller 504. Optionally, a user can define alerts or be automatically alerted in certain situation. Optionally, controller 504 avoids certain activities (e.g., potentially life threatening, as defined, for example, by data-storage there), and requests human approval or instruction.

It is also noted that while controller 504 may be self-sufficient, in some embodiments, some data and/or instruction and/or decision making capability are provided at a separate unit, optionally at a remote location (e.g., at a server or in the cloud).

Reference is now made to FIG. 5B, showing a block diagram of an exemplary embodiment of a volume adaptor in the form of balloon 501, in accordance with some embodiments of the invention. In some embodiments, balloon 501 is expanded and/or shrunk by at least one pump 544. Optionally, balloon 501 comprises fluid, for example gas and/or liquid. In some embodiments, pump 544 is found in fluid communication with reservoir 540. Alternatively or additionally, pump 544 receives gas from the ambient air surrounding the patient. In such embodiments, where the reservoir of fluid is of unconfined fluid, the fluid inside balloon 501 is optionally released through a valve. In some embodiments, the valve is controlled by controller 504.

In some embodiments, pump 544 is found in operative communication with motor 530, which is optionally found in operative communication with controller 504. In some embodiments, motor 530 is found within the balloon device. Alternatively or additionally, motor 530 is found outside the patient and/or is otherwise a separate unit.

In some embodiments, reservoir 540 is found outside the patient. Alternatively or additionally, a reservoir 540 is found within cerebral ventricle 510, optionally in a rigid compartment.

In some embodiments, balloon 501 comprises non-compliant walls. A potential advantage of using non-compliant walls is their inherent limit of expanding, which in the case of a cerebral ventricle, expending too much may cause damage to the patient. In some embodiments, balloon 501 comprises a bilayer, optionally one layer is non-compliant and optionally the other layer is elastic. A potential advantage of using a layer which is elastic within a non-compliant layer is that an elastic layer is possibly more readily changing its volume, while the non-compliant layer determined the limit of the expansion of the elastic layer.

Exemplary Feedback

Figure 5C:
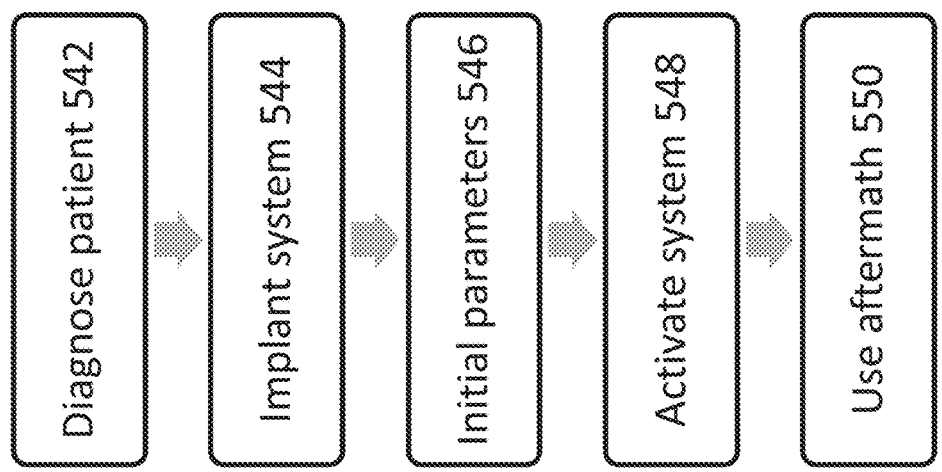
FIG. 5C is a flowchart of a method of using feedback, in accordance with some embodiments of the invention.

FIG. 5C is a flowchart of a method of using feedback, in accordance with some embodiments of the invention.

At 542, a patient is optionally diagnosed. It is noted that different conditions may be treated differently and/or initial setup values may be different (e.g., using a table or other computing function stored in system 500.

At 544, system 500, or at least a volume changing part thereof (e.g., 101) or CSF removing part thereof is implanted in the patient, if not already implanted. Additional exemplary details are given below with respect to FIG. 5D.

In some exemplary embodiments of the invention, implantation includes implanting and/or connecting to one or more physiological sensors, such as intra cranial or intra vascular pressure sensors and/or Doppler flow sensors. Optionally, the sensors are connected to sensor processing circuitries which may or may not be part of system 500, for example, standard sensing systems, such as ICP sensing and measurement systems which may include an ICP probe and generate a digital output encoding a measured ICP. It is noted that an ICP probe may be mounted on expander 101, for example, on or in an introducer catheter thereof, or may be separately provided and/or optionally implanted into the skull via a different opening.

At 546, initial system parameters are optionally selected, for example, using the method shown below in FIG. 5D.

At 548, system 500 is optionally activated, which may include modifying one or more system operation parameters, for example, as described with reference to FIG. 5E. Optionally, the treatment is provided continuously. Optionally, a break is made for measurement, for example, a 1-30 minutes every 0.5-12 hours or every 0.5-4 days, to assess brain status. The break length may be selected to allow for the brain to reach a steady state. In some embodiments, treatment is in sessions, for example, of length 5-400 minutes or longer, with breaks of, for example, 5-400 minutes or longer, therebetween.

At 550, the patient may be weaned from the system/treatment. For example, once the patient stabilizes, ICP goes down and/or based on other indications, the system may automatically, or in response to user input, start reducing or otherwise changing the amount of treatment provided. In one example, the number of treatment sessions (e.g., if treatment is not provided continuously) and/or their length (e.g., length of each session) is reduced and/or intra-session duration increased. Optionally or alternatively, the ratio between treated cycles and non-treated cycles is decreased. Optionally or alternatively, the amplitude of inflation is reduced and/or timing changed, so as to interfere less, or differently in cerebral blood flow. Optionally, a set protocol including stages and different settings and/or goals for the different stages is provided in memory.

In some exemplary embodiments of the invention, the sensing comprises sensing a pulse in the carotid arteries. This has the potential advantage that the timing of the arrival of the pressure wave to the brain is easier to predict and/or less variable.

Exemplary Setup

Figure 5D:
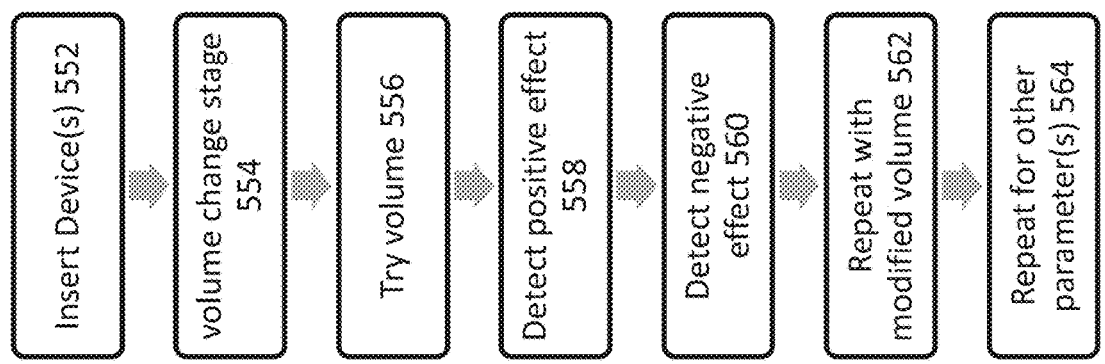
FIG. 5D is a flowchart of a method of setting up a volume adaptor system, in accordance with some embodiments of the invention.

FIG. 5D is a flowchart of a method of setting up a volume adaptor system, in accordance with some embodiments of the invention.

At 552, the device (e.g., volume adaptor 101) is inserted into the brain.

At 554, a constant-volume change process is optionally initiated. As can be appreciated the patient's ICP is typically high. Expanding adaptor 101, may cause an additional pressure spike, which is typically undesirable. In some exemplary embodiments of the invention, CSF is removed from the brain synchronously with or before expansion of adaptor 101, so as to not increase the ICP, or at least not increase by more than a threshold amount, for example, 0.3, 0.7, 1 or 2 mmHg or intermediate or greater numbers. Optionally, the fluid is removed via an external ventricular drainage device. Optionally, adaptor 101 is mounted on such a drainage device and the device is controlled by system 500 to remove fluid as needed and/or to expand adaptor 101 only in accordance with an amount of fluid actually removed by the device.

In some exemplary embodiments of the invention, expansion is provided only during diastole (e.g., low ICP). Optionally, fluid removal is during systole (e.g., high ICP). Optionally, during systole, adaptor 101 is shrunk back to a baseline inflation thereof. Optionally, during introduction, it is not shrunk down to baseline or shrunk down less than baseline. Once the system is used, expansion and shrinking to baseline may be performed.

In one example, the balloon is inserted and inflated to an initial volume of, for example, about 0.5 cc or less. Optionally, during inflation to this volume, CSF is slowly is slowly removed while the balloon is slowly inflated initially to introduce up to a few milliliters of the balloon volume at the expense of CSF volume so that there is no net pressure rise in the process. After this initial inflation, a first deflation and further deflations and inflations (and optionally baseline volume increases) may be prefined without increasing ICP above a baseline.

In some exemplary embodiments of the invention, when augmenting balloon volume, CSF is continued to be drained while the balloon is inflated more. This may prevent ventricular collapse caused by, for example, ICP which is too low, too high or which changes suddenly. It is noted that, in general, the ICP mechanisms cannot differentiate between CSF volume outside the balloon and fluid volume within the balloon (and thus balloon volume). This method may allow higher balloon volume to be reached than simply gradually inflating the balloon and waiting for CSF to redistribute itself in the neural system.

In some exemplary embodiments of the invention, a CSF removal device, such as a catheter with apertures, is used as following, utilizing the native brain pulsation. With every cardiac cycle, in systole, when balloon is deflated, some CSF volume (dCSF) is "pushed" by the brain into the catheter that serves as a conduit, with or without active suction from outside the brain. In diastole the balloon is inflated to its previous set volume plus the volume dCSF (or about) that was expelled by the brain during systole. Net, there is optionally no change in total volume in the brain, except that there is more volume in the balloon and less in the CSF. This may allow the balloon to be inflated and/or deflated to a greater degree.

Thereafter, initial parameters are optionally set up. It is noted that the maximal volume of the device may change during the setup, which may require additional fluid to be removed from the brain during the parameter set up and not only before such set up.

While one or more default system, parameters may be preset, in some exemplary embodiments of the invention, a first stage in use of system 500 is determining parameters that are effective and/or safe. Desirably, a set of parameters which is both safe and effective or which otherwise provides a desired tradeoff between safety and efficacy is determined. Optionally, the default values and/or range limits on one or more parameters, are selected or predefined based on the patient diagnosis. Such values may be stored in a memory of system 500.

A first parameter is volume. Maximal volume of adaptor 101 can determine the highest level of ICP. As noted, high ICP is generally to be avoided. In some exemplary embodiments of the invention, the maximum volume and/or timing of the maximal volume are selected so as to avoid increasing the ICP at times when it is not so desired. It is noted that when referring to ICP, in many embodiments, CCP which relates the ICP to the arterial pressure, may be usefully used instead.

In one method, the maximal volume is selected first and then timing is optimized. Alternatively, both volume and one or more timing parameters are searched for simultaneously.

At 556, a first volume is tried, for example, 0.1 cc or 0.5 cc.

At 558, a positive effect of the volume, for example, increase in CBF or change in dQ/dt (rate of blood exchange), is determined. Such determination may occur over, for example, between 1 and 100 seconds.

At 560, negative effects, for example, increase in peak ICP or reduction in dQ/dt, is determined. Again, this may be detected as a trend over multiple cycles, for example, between 10-200 seconds.

In some exemplary embodiments of the invention, perfusion and/or oxygenation (or other physiological measures such as noted herein) are measured at each volume.

At 562, if the negative effects are too high, volume may be reduced. If the positive effect is too low, volume may be increased (e.g., by 0.1 cc or other small amount such as between 0.05 cc-0.17 cc). Optionally or alternatively, other parameters may be changed, for example, one or more timing parameters, to change the part of the cardiac (and/or ICP) cycle that maximum volume overlaps with.

It is noted that setup can include two or more sets of parameter values, for example, a desired maximum volume and a second, higher "allowed" volume which may be associated with certain patient conditions (e.g., for manual or automatic application and/or caretaker alert generation) and/or be allowed to be applied for certain time durations (e.g., intentionally or unintentionally, as may happen for timing).

At 564, other parameters may also be evaluated in a similar manner. It is noted that while a single parameter search process is described, search methods and optimization methods, such as gradient descent, which optimize/search over multiple parameters simultaneously or in an interleaved manner, may be used as well.

One or more of the following system parameters are optionally varied:

(a) start expansion;
(b) End expansion;
(c) Maximum expansion volume or change in volume;
(d) Rate of volume change;
(e) Shape of slope of volume change;
(f) Length of plateau;
(g) Slope of plateau or other non-linear shape of plateau;
(h) Start deflation;
(i) Deflation rate;
(j) End deflation;
(k) Deflation slope;
(l) Deflation plateau and/or duty cycle of inflation & deflation plateaus;
(m) delay between inflation and deflation
(n) minimum (baseline) of expansion
(o) Pressure or system compliance at any or all parts of ICP cycle; and/or
(p) Physiological parameter (e.g., R-wave detection, blood pulse wave) to use for timing of each event; and
(q) number of pulses in a cycle (described below), each pulse possibly having different values for any or all of the above parameters.

Experiments in a swine model were performed, some of whose results are also shown in FIGS. 12A-C, 13A-B and 14A-B, and which also inform some indication as to possibly useful starting points for some or all of the above settings and/or ranges to be searched during search or adjustment.

The Experiments were performed on swine (40-50 kg), which were anesthetized intubated, and laid supine for carotid artery catheterization. Thereafter the swine we moved to a prone position for a Cranial incision with implantation of an ICP monitor, performance of Ventriculostomy and installation of a CBF monitor and a balloon, as described herein. The location of the balloon and Ventriculostomy were validated by ultrasound.

After confirmation stability, a first group of 5 swine was treated to be a Water intoxicating model (infusing 0.18% saline intravenously slowly causing severe hyponatremia then brain edema causing a gradual increase in ICP. A second group of 5 swine had an extremely slow infusion of normal saline into ventricles of the brain causing gradual hydrocephalus. In both groups, ICP gradually increased and the balloon device was tested and shown to be generally effective at the following ICP steps: 10-15-20-25-30-35-40 mmHg. The swine were hemodynamicly stable, and the results were of the same general nature for both sets of swine. Some results are shown herein to illustrate some embodiments of the invention. It is noted that a large volume may be needed for treating a human brain than a swine brain, but the swine brain is considered to be a useful model for human brain with respect to ICP and flow problems.

In some exemplary embodiments of the invention, the inflation and/or deflation of a balloon is short, for example, about 10-20 ms for a volume of between 0.5 and 2 cc. Optionally, a syringe pump is used with a speed of, for example, 2000 cm/sec movement of the piston thereof. Optionally, maximum speed is limited by a desired to avoid jolting the brain.

In some exemplary embodiments of the invention, it is noted that below, for example, 0.6 cc there may be no effect. Optionally, the volume is at least 1.2 cc or even at least 1.8 cc. In general, a larger volume appears beneficial (providing it does not cause a too high ICP). As noted, the volume may be adjusted as needed during treatment, optionally automatically.

In some exemplary embodiments of the invention, the baseline volume of the balloon (or other expandable structure) is selected to allow a working volume even if ICP increases. It is noted that in some embodiments, an important function of the balloon is its deflation, and it may be desirable to ensure maintaining such potential. In some exemplary embodiments of the invention, the initial removing of CSF allows the balloon to be inserted and inflated to such initial baseline volume without significant effect on ICP. For example, such baseline may be 0.5, 1, 1.5, 2, 2.5 cc or smaller or intermediate or larger volumes (e.g., having a baseline of 2 cc and an inflation volume of 1-2 cc in addition).

Optionally, such baseline inflation allows the device to occupy space even if there is ventricular collapse. Optionally, during ventricular collapse (which may be short term or episodic), the baseline of the balloon may be allowed to decrease, so as to use the difference between the old baseline and the decreased baseline as a volume for expansion. Optionally or alternatively, during ventricular collapse operation of the system may be stopped, however, there will be no need to reintroduce and inflate the balloon.

In some exemplary embodiments of the invention, the balloon is inflated and deflated at other times during the ICP cycle, optionally to a lesser amount, for example, to maintain expansion volume for the balloon.

In some exemplary embodiments of the invention, synchronization is selected to be with the R wave of the cardiac cycle, or an indication of carotid pulse or other artery near the cerebral arterial system. This may be the basis for all the timing parameters, for example, as described below. Optionally, if the heart rate changes, times are adjusted accordingly, optionally automatically. Some parameters may be independent of HR per se (e.g., deflation duration) and some may be linked to particular parts of the R-wave (e.g., deflation start before systole). Adjustment can be, for example, pro-rate or at fixed timing relative to such events.

For example, a user may select a timing based on the ICP and the system can automatically calculate the delay between an ECG signal or an arterial pulse and this point in the ICP wave. Optionally, the system also takes into account a rate of volume change of expander 101. In one example, the system is setup using carotid pulse (e.g., using a Doppler sensor) and then the time between an ECG feature, such as R wave and the carotid pulse is measured so that the timing can be based on ECG.

In some exemplary embodiments of the invention, deflation is set to start with the ascent of the arterial pressure rise in the carotid artery. In swine, this was found to correlate to approx. 50 milliseconds post R-wave detection from the swine ECG. Optionally, after such setting, the system is checked (e.g., relative to ICP or arterial waveform) to ascertain that indeed the deflation occurs just at the beginning of the pressure rise, preferentially just prior to it. Optionally this test is applied before the system is activated (e.g., FIG. 5E).

In some exemplary embodiments of the invention, adaptor 101 expansion is set to happen during diastole. Experimental evidence suggests that inflation during systole causes a decrease in perfusion and increase in ICP.

In some exemplary embodiments of the invention, a test to be applied before system activation includes confirming that inflation occurs only after peak pressure has passed and optionally when systole is completed.

In some exemplary embodiments of the invention, inflation is selected to occur as close as possible to the deflation of the next cycle, which is generally very late in the diastole of the cardiac cycle. As close as possible does not mean that inflated state duration is approximated to zero in every case, for example, there may be (patient dependent) a minimal duration of the inflated state so as to assist in fluid excavation from the brain. This may be determined by modifying the duration and monitoring CBF or one or more other parameters.

In some exemplary embodiments of the invention, the following setup and parameters are used: R-wave detection, then calculation of the cardiac cycle (example: Heart rate 75, cardiac cycle of 800 milliseconds.) Then selecting R wave latency for deflation (for example, 50 ms depending on arterial waveform and/or deflation rate). Then the R-R segment is detected (e.g., 800 ms in this example), and subtracting, for example, 50-100 ms to define an inflation point. This results (for a 800 ms cycle), in inflation starting at 50 ms and deflation starting at 700 or 750 ms. The time to inflate and/or deflate is optionally between 10-20 ms.

Based on experimental results, these timing parameters appear to be a useful set, at least for some patients, for example, having an initial ICP of 25-30 mmHg, initial perfusion (hemdex monitor)=20-30 cc/min/100 gr tissue. Volume can be, for example, between 1.5 and 3 cc. For example, in a swine model, post activation of system 500, perfusion increased by 3-5 cc/min/100 gr tissue and ICP was reduced on average by 10%-15% (e.g., 25-30→20-25).

Exemplary Use of Feedback During Treatment

Figure 5E:
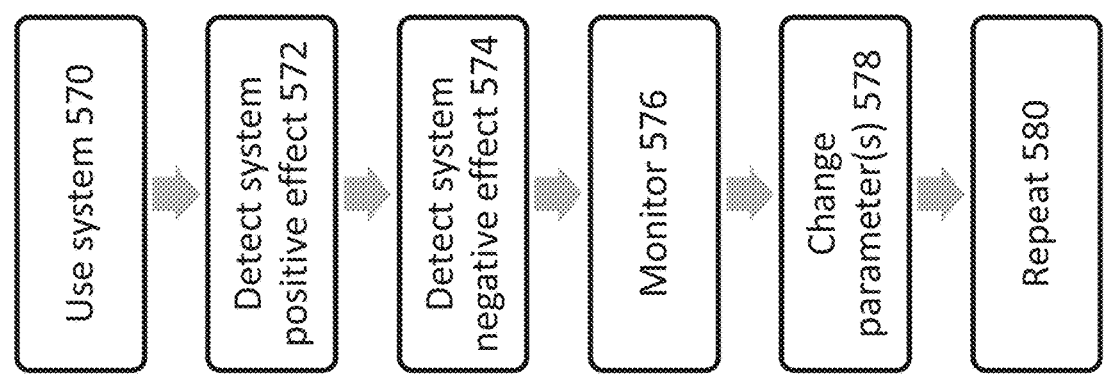
FIG. 5E is a flowchart of a method of adapting one or more parameters of a volume adaptor system, in accordance with some embodiments of the invention.

FIG. 5E is a flowchart of a method of adapting one or more parameters of a volume adaptor system, in accordance with some embodiments of the invention.

At 570, system 500 is used, for example, using parameters set according to FIG. 5D. As can be appreciated, not only does the patient's condition typically change over time, there also may be short-term physiological variations. In some exemplary embodiments of the invention, system 500 is adaptable to one or both of long-term changes in patient condition and short-term changes in physiology.

A first type of adaptability is avoiding and/or reducing harm. A second type is increasing and/or maximizing benefit.

In a simplest example, changes in a patient's cardiac cycle can invalidate parameter selection. In another example, gradual increase or decrease in baseline ICP can cause a need or allow for an opportunity to change maximum volume and/or inflation/deflation durations.

While system 500 is in use, one or more measurements of a patient's condition and/or response to treatment are optionally monitored.

At 572, a positive effect of system 500, for example, increase in CBF, is optionally detected. Lack of a positive effect and/or decrease in positive effect may suggest a change in parameters.

At 574, a negative effect of the system, for example, a reduction in CBF or increase in peak ICP, are detected. Such a negative effect may suggest a change in parameters.

At 576, monitoring of parameters of system 500 and/or the patient may suggest that system parameter change may be beneficial, for example, if baseline ICP went down, volume increase may be acceptable.

At 578, one or more system parameters may be changed. Optionally, the change uses predefined sets of changes (e.g., simultaneous change in volume and deflation delay). Alternatively, only one parameter is changed at a time. Optionally, a search method, for example, as described with reference to FIG. 5D may be used.

It is noted that a patient may have several sets of system parameters and/or corresponding sets of allowed or desirable physiological parameters. Optionally, 572-576 may be used so that at 578 a different set of system parameters is selected, for example, (manually or automatically) in response to a set of measured or desired physiological measures. Optionally or alternatively, a certain amount of leeway is provided by such sets, for example, a certain percentage of cardiac cycles with no increase in perfusion relative to a baseline may be allowed, if also ICP is kept lower.

In one example of adaptive treatment, CPP and/or an integral of ICP over time is used as a physiological measure.

In some exemplary embodiments of the invention, a user can provide input such as limits, desired values, values at which to alert and/or values considered to be therapeutic.

If such measures do not show (any and/or sufficient, for example, 10%) improvement over baseline and/or over some other setting (e.g., an expected improvement or a feared-for degradation), system parameters may be changed. In one example, maximum volume is gradually increased. For example, lack of improvement over 5 minutes, triggers an increase in maximum inflation of 0.1 cc. decision on changing may depend, for example, on a baseline rate, such as a few minutes and/or on a severity of an effect, for example, large adverse effects (e.g., as defined by system settings) causing a rapid reduction in maximum volume.

If change in volume (e.g., until a maximum safe value is reached) does not provide the desired improvement, inflation and/or deflation times are changed, for example, at 1 ms steps relative to the R wave. Optionally, the size of the step varies, for example, starting large and then getting smaller and/or changing in direction according to the effect of the change.

Detection of adverse effects optionally trigger reduction of the expansion volume, for example to a baseline amount or lower. If this is not enough, the inflation may be advanced in time relative to the R-wave and/or change in timing (e.g., length) so as to not coincide with ICP above a certain value and/or percentage of peak ICP.

In a particular way of using an ICP integral, the ROC of the ICP(t) curve per cardiac cycle (or set of cycles) is compared to a previous cardiac cycle (or set of cycles) and defines the ROC dose to be allowed and/or provided.

Optionally, such comparison uses matched cycles, for example, non-arrhythmic cycles, similar HR cycles, similar ECG cycles and/or cycles that do not have arrhythmia.

In some exemplary embodiments of the invention, system 500 is adapted relative to a surrogate marker. For example, system 500 is adjusted in real-time with respect to any relevant proven perfusion or acceptable brain oxygenation monitoring method (e.g., CBF monitoring, PbtO2 monitoring etc.) and/or running ICP/CPP dose calculated realtime integral (CPP(t) or ICP(t)) as a feedback in respect to the system timely activation or inappropriate activation, for example, as described above.

Optionally, within 1-600 seconds of system activation a value of the chosen marker is analyzed and used for later activation. Optionally, between 60 and 3000 seconds of data are collected before activation and/or during a low-grade activation (which may not have a positive effect, but also no negative effect) and used as a baseline.

If the outcome is worse after activation as compared to this baseline, synchrony is optionally checked and/or optimized. For example, deflation timing may be checked (optionally manually). Optionally or alternatively, inflation time is checked and/or modified (e.g., in small time steps, for example, back to a short time, such as 30 ms, after peak pressure), backwards in time. Optionally, a perfusion (or other) marker is used to determine eth effect of such change in inflation time and/or in deflation time. Once improvement is detected, these may be used as the new parameters and/or as a point for starting an optimization process of other parameters.

Figure 12A:
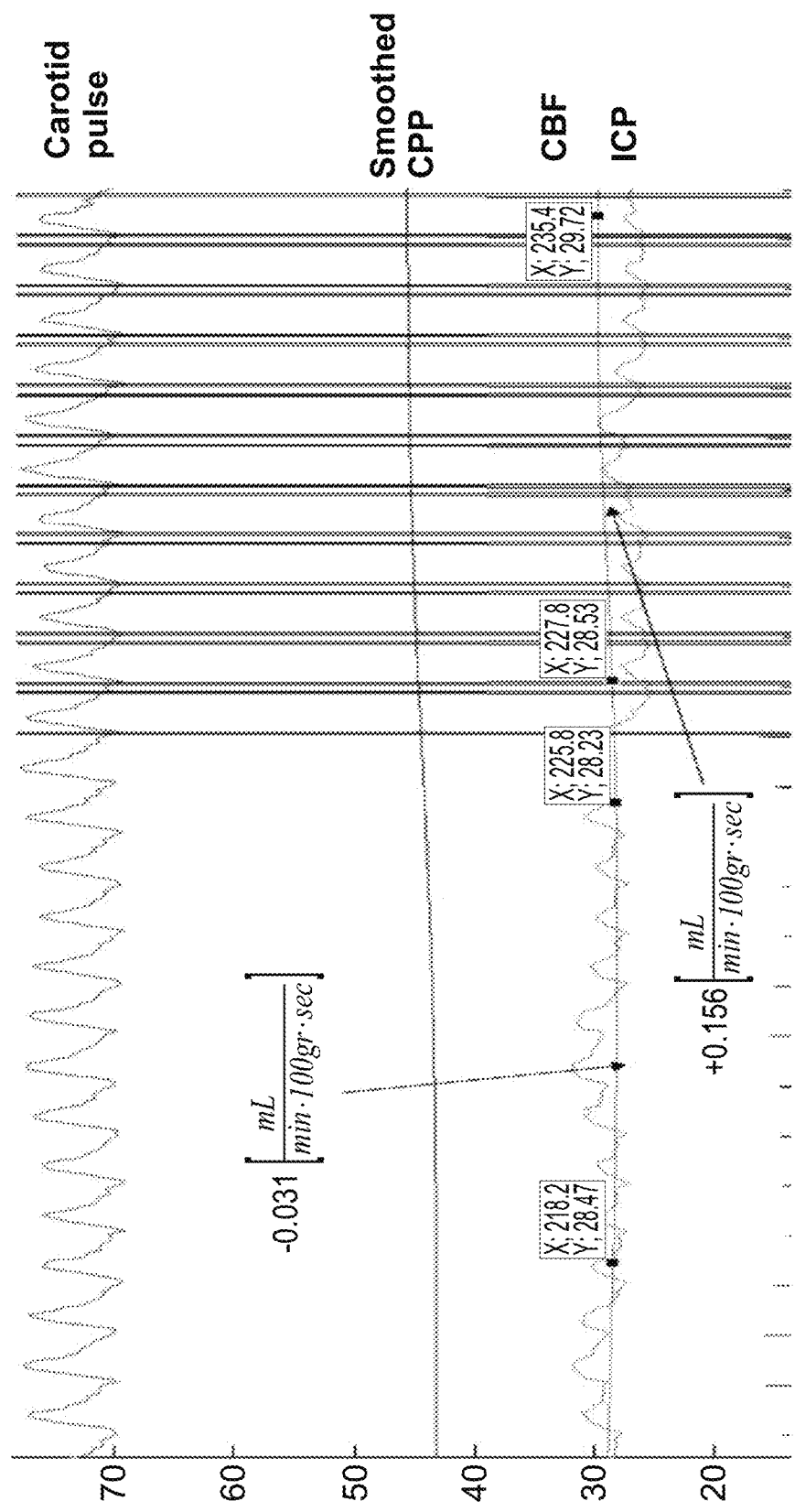
FIG. 12A is a graph illustrating using dQ/dt for evaluation of CBF change as an indicator, in accordance with some embodiments of the invention.
Figure 12B:
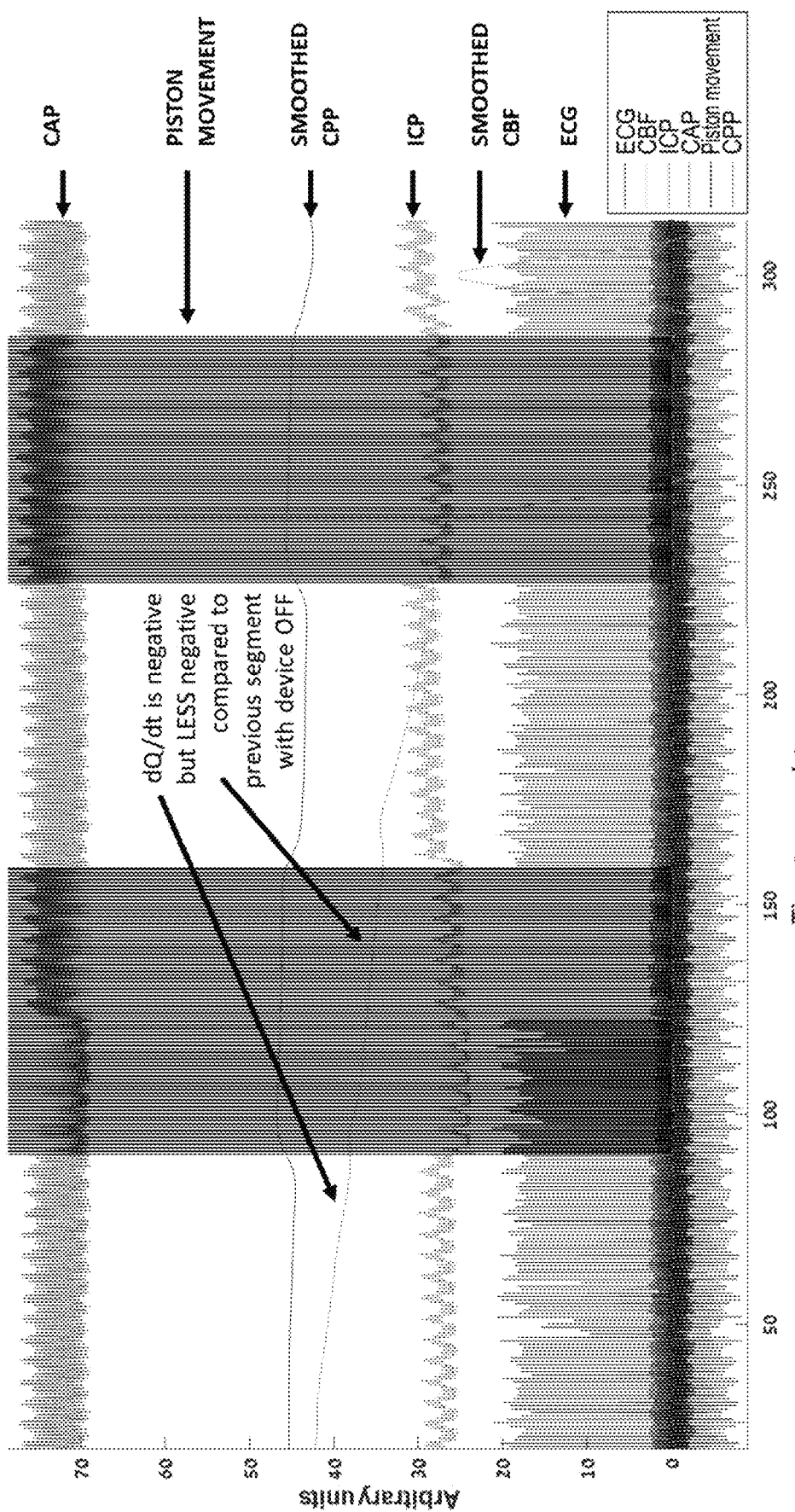
FIG. 12B is a graph illustrating using dQ/dt for evaluation of CBF change as an indicator, in accordance with some embodiments of the invention.
Figure 12C:
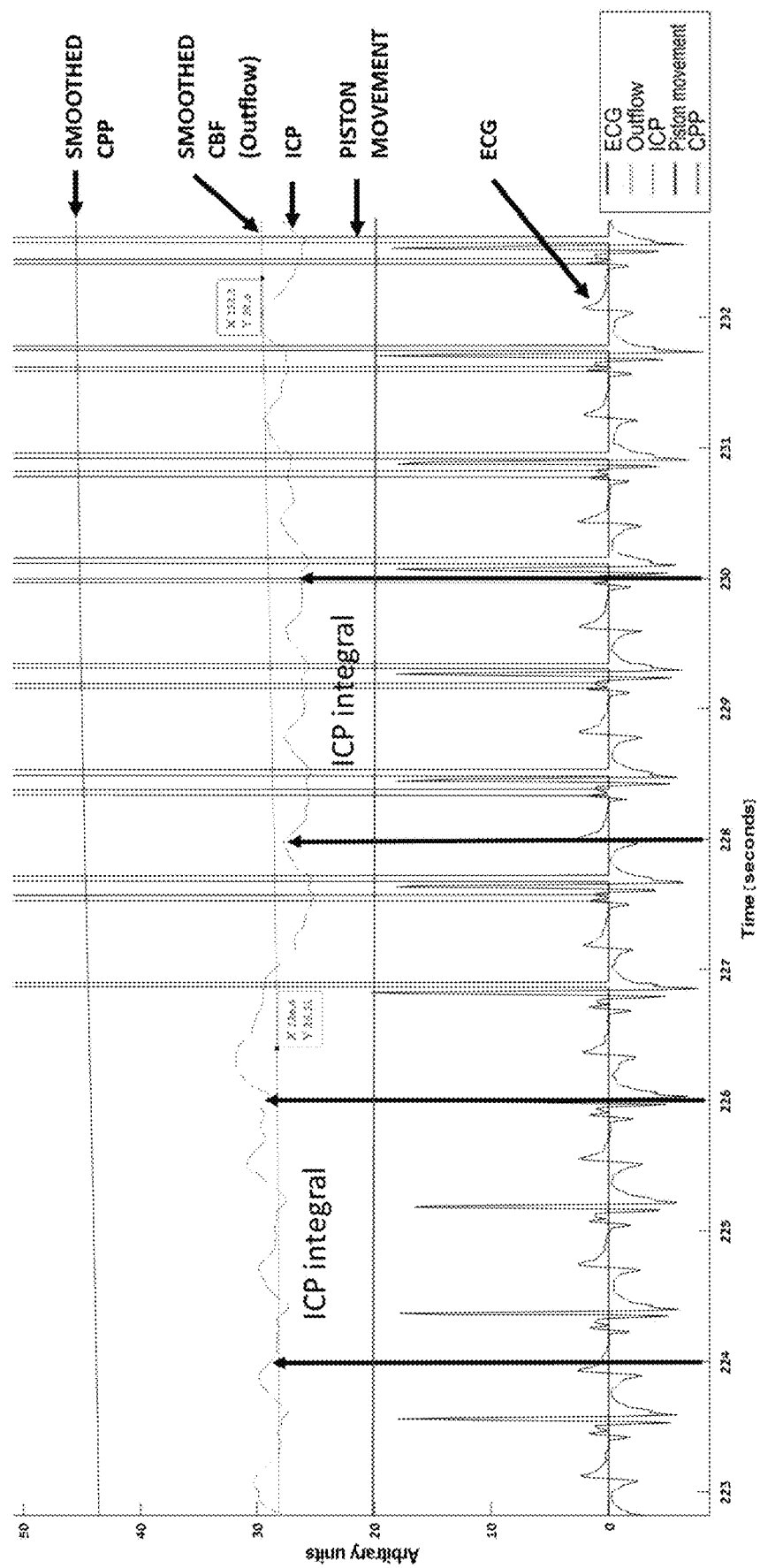
FIG. 12C is a graph illustrating using ICP(t) integrated over time for evaluation of system efficacy, in accordance with some embodiments of the invention.

FIGS. 12A-12C show exemplary ways of assessing efficacy of use of system 500, in accordance with some embodiments of the invention.

FIG. 12A shows assessment by dQ/dt in a swine model. The vertical lines indicate when the balloon was inflated or deflated (deflation being just before systole). As can be seen, dQ/dt increased and also changed direction from −0.031 to +0.156 ml/(min*100 g*sec) after system operation.

FIG. 12B shows an example where dQ/dt did not become positive, but still increased.

FIG. 12C shows an example where an integral (e.g., over time between consecutive vertical arrows) of ICP is used. Respiratory artifacts were removed and the vertical lines indicate balloon inflation/deflation events. As can be seen, the ICP integral goes down when the system is in use. Similar results are expected for integral of CPP.

In some exemplary embodiments of the invention, instead of using thresholds (or other methods of comparing values to detect change) in desired values, morphology is used. For example, if a goal of treatment is to increase a duration of low ICP time during diastole, or to flatten or split a peak ICP pressure during systole this can be detected by morphological analysis of the ICP wave. FIGS. 13A-B Show examples of such effects. Morphological changes may be detected, for example, using template matching or by calculating a distance between the existing and a desired morphology. Various methods of comparing morphologies and/or detecting changes the morphologies of 1D signals are known in the art and may be used.

In some exemplary embodiments of the invention, the goal function of the treatment may include a plurality of different physiological measures. Optionally, a composite score is made of these measures and treatment adjusted to result in a physiological state with a score corresponding (e.g., reaching, exceeding) this composite score.

At 580, the process of adjusting and using system 500 is repeated. It is noted that if adjusting fails and/or the patient exceeds safe boundaries, a user (e.g., physician) may be alerted, for example, using light, sound and/or an electronic message. In some cases, adjustment is performed manually, and a user may be alerted to approach the system and provide input (e.g., carotid Doppler sensing), as part of an adjustment procedure.

In some exemplary embodiments of the invention, instead of looking at an integral over time, what is looked at is a derivative, for example, change in flow as a function of time. An increase in this indicator, for example, may indicate a functional improvement, even if it does not manifest in a change in ICP and/or CBF and/or perfusion. In some exemplary embodiments of the invention, it is noted that CPP may provide a better indicator than ICP which may depend on other physiological parameters. Optionally, CPP is used rather than ICP for some or all of the methods described herein. It is noted that measures described herein for use for adjustment may also be used for patient monitoring (e.g., displayed to a user or sent to a patient or hospital information system) even if not adjustment is practiced.

In some exemplary embodiments of the invention, it is noted that the brain is part of several feedback loops. In one example, changes in CBF may case a change in carotid (or other arterial) blood flow. Optionally, what is used as feedback for system 500 adjustment includes such measures in addition to or instead of actual measurements on the brain, as an indication that a positive or negative effect is occurring.

Some Exemplary Timing Considerations

Following are some exemplary considerations for timing, in accordance with some embodiments of the invention.

In some exemplary embodiments of the invention, the timing is based on events. Optionally, the event is R-wave detecting in an ECG, and the timing of activation of parts of system 500 is based on time delays relative to the R-wave and/or an expected next R-wave. Optionally, a different even is used, for example, onset of a pressure pulse in the carotid or other artery, optionally an artery near the brain.

In some exemplary embodiments of the invention, deflation is specifically and preferentially set to start with (e.g., within 10-20 ms thereof) the ascent of the arterial pressure rise in the carotid artery. In a swine model, this was found to be about 50 milliseconds post R-wave detection from ECG.

In some exemplary embodiments of the invention, once deflation time is according to ECG, it is checked against arterial pressure, for example, for a short time and/or for a range of ECG morphologies. Optionally, what is checked for is that deflation begins and/or ends before pressure increase. Optionally, as a safety feature, system activation is blocked if this timing is not found. Optionally, instead of using arterial pressure to detect no-compliance, the timing relative to ICP systole is used to detect non-compliance.

In some exemplary embodiments of the invention, a safety check (e.g., of a similar type—based on actual pressures) is made to ensure that inflation occurs during diastole and/or when ICP is low.

In some exemplary embodiments of the invention, what is desired is that inflation be as close as possible to deflation. Optionally, a short period (e.g., 10-100 ms, for example, 5-50 ms, for example, 3-30 ms) of inflated balloon is provided to allow the intra-cranial fluid(s) to respond to the inflation. Optionally, the inflated state duration is long enough so that when deflation occurs, fluid (e.g., CSF, venous blood) that was displaced by inflation does not compete too much with incoming arterial blood. For example, at least 20%, 30%, 40%, 60%, 80% or intermediate percentages of flow increase due to deflation of the balloon should be due to arterial blood. Optionally, this is monitored and/or evaluated using imaging, for example, using MRI imaging or using Nuclear medicine imaging, for example, using suitable PET isotopes in the blood, or by detecting a first blush of x-ray contrast material, using x-ray imaging. Alternatively, this may be detected by checking the overall outcome, such as CBF.

This has two potential benefits. First, ICP may be lowest at this time. Second, the balloon is inflated for as a short a time as possible and so interferes with the brain as little as possible.

Figure 5F:
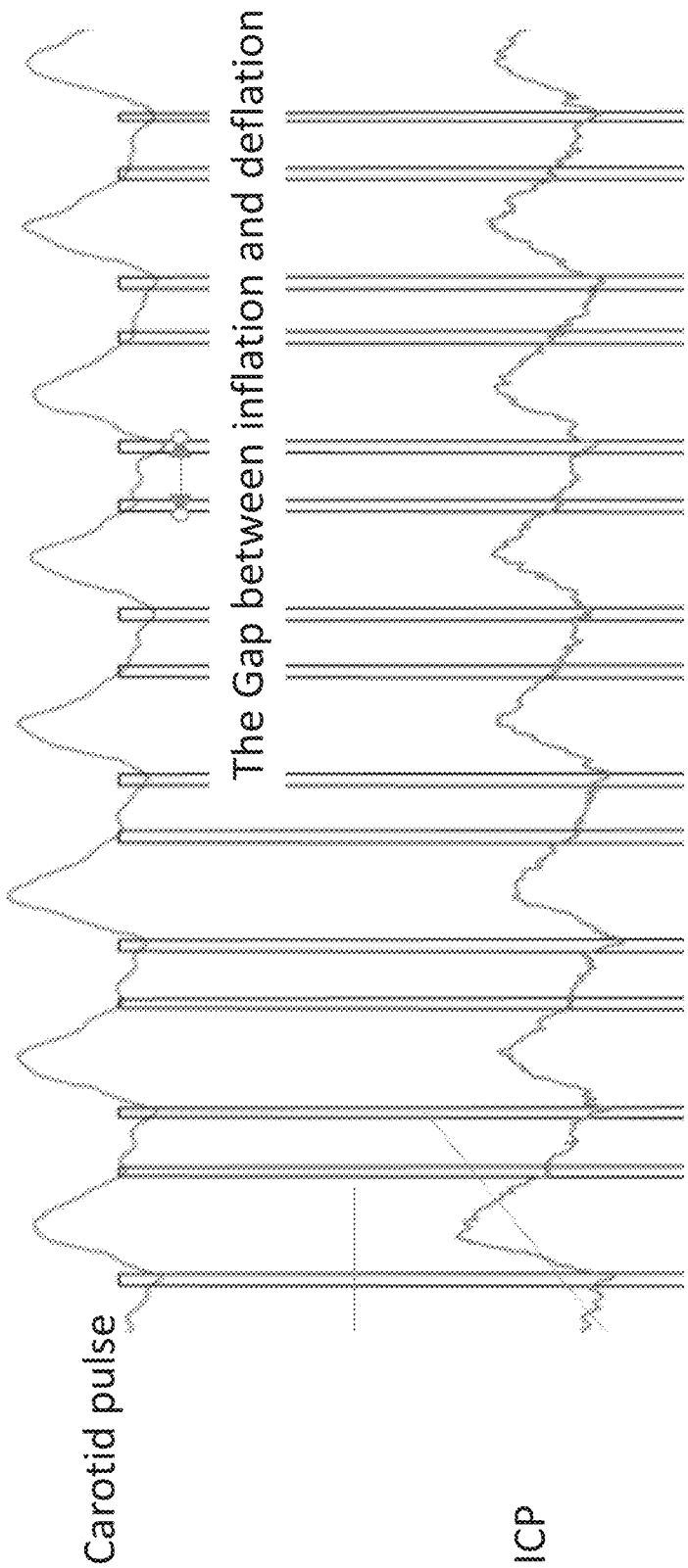
FIG. 5F is a chart showing an exemplary timing of a volume adaptor system, in accordance with some embodiments of the invention.

FIG. 5F shows an exemplary delay between inflation and deflation, in accordance with some embodiments of the invention. Optionally, the deflation time is set (e.g., taking into account variability) to be before systole starts and the inflation time is set to be after systole ends, but optionally, as noted above, as close to deflation as possible. Optionally, inflation may start after the R-wave is detected.

In some exemplary embodiments of the invention, this results in a low or very low duty cycle for the balloon, with the balloon being inflated less than 50%, 30%, 20%, 10% or intermediate percentages of the cycle (e.g., cardiac or ICP). In some exemplary embodiments of the invention, multiple pulses are provided in a cycle. Optionally, the total duration of inflation during a cycle is still within these ranges.

In some exemplary embodiments of the invention, a composite score is optimized which is composed of both balloon volume and balloon inflation state duration, for example, a product of the two. In use, volume is set as described herein and initial inflation state duration is set to between, for example, 50 and 70 ms. This duration is slowly reduced (and volume optionally increased) according to an effect on a desired measure (e.g., CBF, CPP integral, etc.). As can be appreciated different disease states and/or pressures may indicate a need for different inflation durations. Optionally, system 500 is preprogrammed with a set (e.g., in memory) of disease condition and suggested starting points, ranges, signals to be sensed, desired results and/or expected results, associated with each one. Indication by a user (or based on values of various parameters and/or responses to system 500 manipulation, by circuitry), may be used to identify a disease state and suggest one or more parameters to be varied and/or sensed.

In some exemplary embodiments of the invention, the deflation is timed to be within 10-50 ms (or less, possibly with an overlap with the upstroke) before systolic upstroke and inflation is timed to be in the last third of the cardiac cycle (e.g., typically between 150 and 330 ms before the systolic upstroke).

FIG. 13A shows an example of the effect of a good timing on brain condition, in a swine model. As can be seen, CBF increases after activation, at parameters of 1.8 ml volume change, deflation 90 ms after R-wave (HR=~75 BPM), inflation 500 ms after r-wave and ICP 28 mmHg. Also noticeable is an increase in diastolic downwards spike and a flattening and/or splitting of the peak ICP. Also noticeable is an ICP reduction. It is noted that the inflation state duration is apparently about 210 ms.

FIG. 13B shows another example of the effect of a good timing on brain condition, in a swine model. As can be seen CPP increases after activation and ICP decreases, at parameters of 1.8 ml volume change, deflation 90 ms after R-wave, inflation 590 ms after r-wave and ICP 34 mmHg. Also noticeable is an increase in diastolic downwards spike and a flattening and/or splitting of the peak ICP.

As can be appreciated, which parameter to use as a guide for treatment is often a decision made by a caretaker. However, a default may be programmed into system 500.

FIG. 14A shows the effects of bad timing, in this case deflation at 420 ms and inflation at 650 ms, for a (low) volume change of 1.2 ml. As can be seen, ICP peak shape changes, but does not noticeably reduce. This may be due to an overlap of inflation with the systole and/or late onset of deflation. FIG. 14B is a longer-time view, showing the effects of bad timing. As can be seen, CBF goes down and improvement in CPP stops. This may be due to an overlap of inflation with the systole and/or late onset of deflation.

In some exemplary embodiments of the invention, the parameters for treating increased ICP include, inflation between −400 and +50 ms relative to R-wave; deflation between −50 and +90 relative to R-wave; inflation/deflation rate between 5 and 300 ms (optionally 5-50 ms) to maximal volume change and volume change of between 1 and 4 cc. It is noted that in some embodiments, what is controlled is not balloon volume change, but rather balloon pressure, optionally selected to remain below peak ICP. Optionally, during deflation, fluid is removed from the balloon based on volume considerations, rather than pressure considerations (e.g., 2 ml fluid removed, rather than reducing balloon pressure to 25 mmHg).

Multiple Pulsation Modes

In some exemplary embodiments of the invention, more than one pulsation is provided per a cycle. For example, two or more pulsations may be provided. Some examples of two pulsations include: inflation and then deflation and then again inflation and followed by deflation; inflation and then a first deflation and then a second deflation; or inflation and then another inflation and then deflation.

From a functional perspective, a pulse may be inverted: first deflation and then inflation. Similarly as the pulses are often applied every cycle, part of a pulse may overlap with a different cycle than another part of the pulse.

Also, it should be noted that while a pulsation (or more than one) may be applied every cycle, in some embodiments, the application is for fewer than all cycles, for example, skipping cycles where the R-wave (or other timing event is not correctly detected), skipping cycles after certain negative or positive indications are seen in the feedback (e.g., decrease in CBF) or an overall protocol which defines that pulses not be applied every cycle, for example, every other cycle or using some other sequence. Optionally, the frequency of treated cycles is increased at a start of a treatment nd/or decreased at an end of a treatment. Optionally, the balloon is deflated between pulse applications. Alternatively, the balloon may be in an inflated state.

In some exemplary embodiments of the invention, the pulsation (inflation and then deflation) for improving systolic uptake is provided and an additional pulsation is provided as well. Optionally, this additional pulsation is provided after the systole is completed, or at least mostly completed and optionally within the time between the middle and last third of the diastole. In some exemplary embodiments of the invention, the timing is selected to occur when blood moves into the venous space (and thus does not help perfusion) and starts draining towards the sinuses. It is noted that the sinuses are generally not affected by ICP. The additional pulsation is optionally timed and/or has a volume and/or other parameters so as to urge blood into the sinuses and, upon deflation, allow blood flow (e.g., via arterioles) to perfuse the brain.

In one example, the balloon is inflated for a short period of time (e.g., 5-50 ms) causing abrupt increase in ICP in the diastolic phase propelling venous blood outside the intracranial system, and then the balloon is deflated. Then the systolic pulsation is optionally applied—late diastolic inflation followed by pre-systolic deflation. The systolic pulsation may include, for example, an inflation state duration of 10-30 milliseconds.

In some exemplary embodiments of the invention, the added diastolic inflation/deflation cycle is set up to evacuate venous blood from the brain, by exploiting the coupling between the ICP and the venous vasculature—where slightly elevated ICP can compress the veins, but is not sufficient to compress the arterial system. Since the venous sinuses are enclosed in rigid incompressible spaces, despite elevated ICP no collapse occurs at the exit point so venous blood can flow out of the body, but cannot reflux back to the brain once the blood has left the brain, as the arterial system (and the brain) has high resistance and high pressure. One potential desirable result is that more volume is available for oxygenated blood flow. Optionally, this determined the volume of this pulsation which is optionally selected to elevate ICP (can be determined during setup) to, for example, 15-25 mmHg or more, in order to achieve instantaneous squeezing of the venous bed (which is open due to the sinuses which are stiff). While in some embodiments deflation is to the baseline value, in some embodiments, deflation is not to the baseline value, which may assist in preventing venous backflow.

In some exemplary embodiments of the invention, search and adjustment, e.g., optimization, for example, during setup and/or use of the system use an additional sensor to estimate the effect on venous flow. For example, a sensor measuring venous pressure as close as possible to the cerebral venous vasculature (e.g., a jugular venous pressure monitor, or a central venous pressure monitor or a direct sinus pressure measurement) is provided and its measurements used as a marker to choose pulse parameters, such as timing and volumes.

In some exemplary embodiments of the invention, the total duration of inflation state in all pulsations is maintained short, for example, less than 100 ms, for example, between 30 and 60 ms, or less.

As noted, the number of pulsations as well as other properties thereof may be selected during setup and/or on an ongoing basis, manually and/or automatically.

It is also noted that in some embodiments (e.g., for patients with certain disease states) it may be desirable to always or sometimes omit the systolic pulsation, but maintain the diastolic pulsation, or vice versa.

Figure 5G:
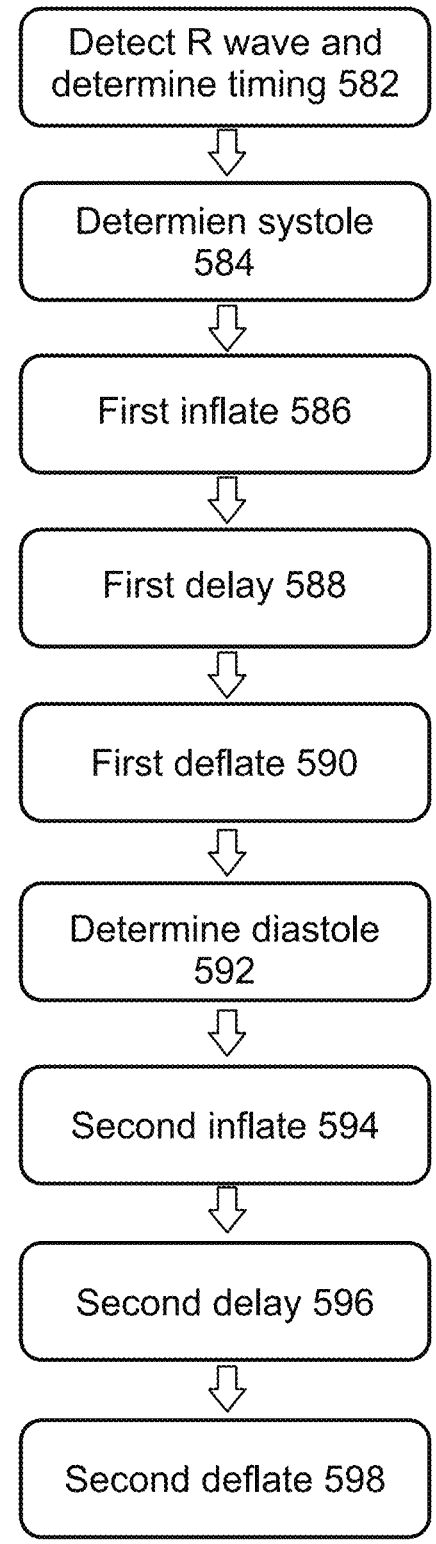
FIG. 5G is a flowchart of a method of multiple pulsations per cycle, in accordance with some embodiments of the invention.

FIG. 5G shows a process of applying two pulsations, in accordance with some embodiments of the invention.

At 582, a physiological event, such as R-wave is optionally detected and various timing parameters are set. In some embodiments, the balloon inflation is controlled directly by a detected physiological event and times relative thereto, without the need to predict future events, for example, if there is time from R-wave detection to decide and apply balloon deflation.

At 584, the systole time is optionally determined (e.g., using a detected R-wave and R-R delay) so as to calculate when a pre-systolic inflation is to be performed At 586, a first inflation of the balloon is carried out At 588, a first delay is activated, during which the balloon remains inflated, in an inflation state.

At 590, the balloon is deflated, e.g., just before systole.

At 592, the diastole is optionally determined, optionally using a sensor for determining safety of the second pulsation and/or simply by time calculation.

At 594-598, the second pulsation is applied, optionally using different parameters than the first pulsation.

Figure 5H:
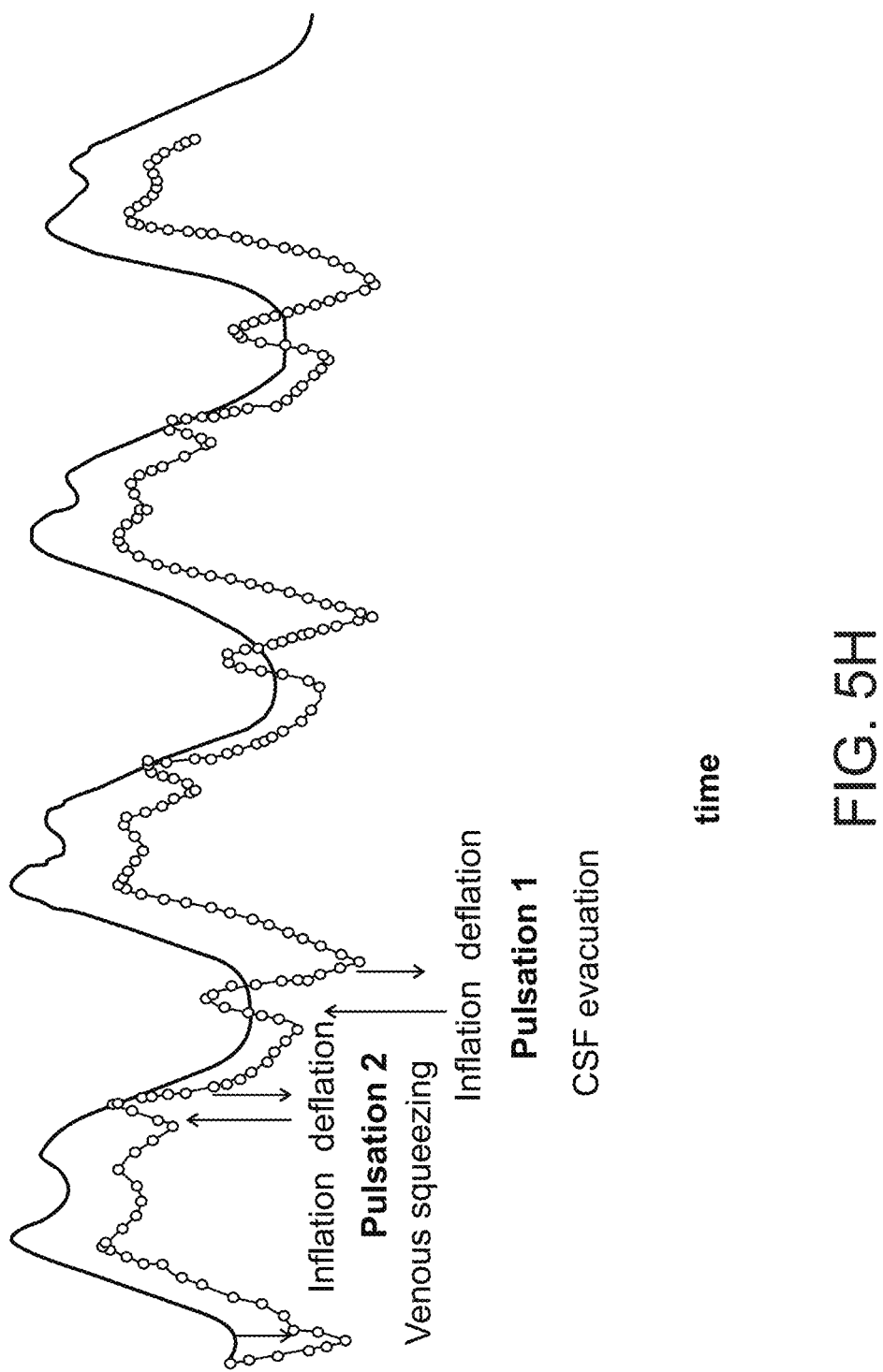
FIG. 5H is a chart showing a simulation of an effect of double pulsation of a volume adaptor system, in accordance with some embodiments of the invention.

FIG. 5H shows the timing and expected effect of a second pulsation as a dotted line, with a solid line showing the expected effect of a single pulsation. As can be seen, while ICP increases, it need not increase to past a maximum value during the systolic ICP peak. Possibly, the final ICP before the systolic increase, is lower due to the double pulsation. This effect may be useful in addition to or instead of the effect of better perfusion due to venous squeezing. Possibly, the use of double pulsation will cause an overall reduction of ICP as shown, at most parts of the ICP cycle.

Exemplary Device for Influencing Cerebral Perfusion Pressure

Figure 6:
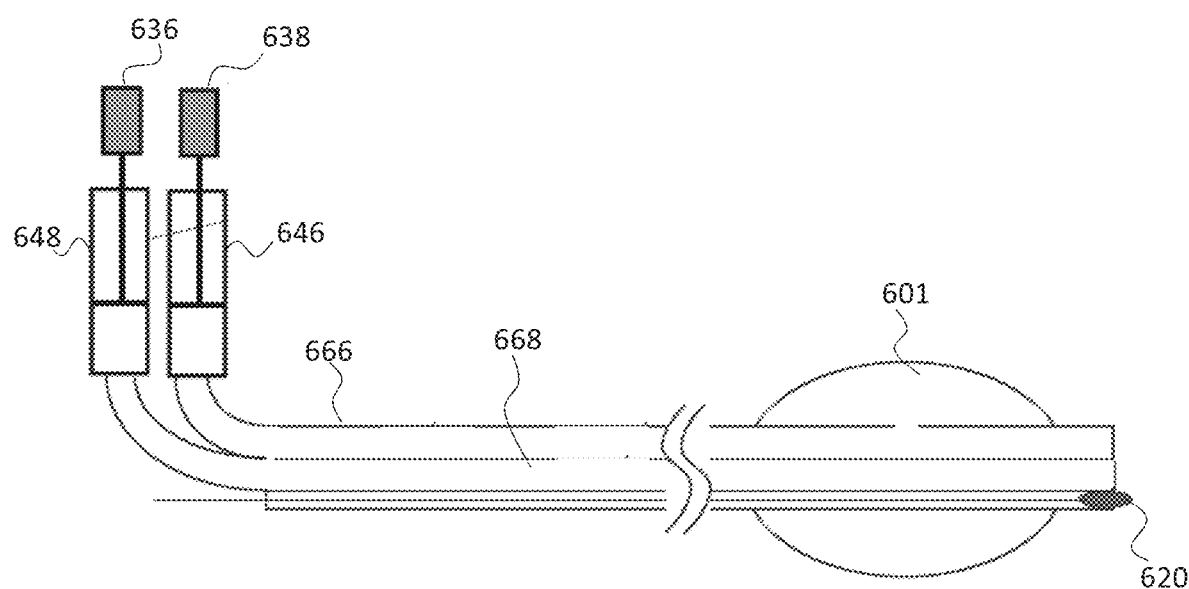
FIG. 6 schematically illustrates an optional device for influencing cerebral perfusion pressure in the form of a balloon, in accordance with some embodiments of the invention.

Reference is now made to FIG. 6, schematically illustrating an optional device for influencing cerebral perfusion pressure in the form of a balloon, in accordance with some embodiments of the invention.

In some embodiments, volume adaptor is provided in the form of balloon 601. In some embodiments, balloon 601 is comprised at a distal end of a catheter. Alternatively or additionally, balloon 601 is comprised at a distal end of an external ventricular drainage device, wherein the distal end is the end within the brain. Alternatively or additionally, balloon 601 is in fluid communication with at least one tube, optionally a suction tube 668 and/or an inflation tube 666. In some embodiments, the tube is connected to at least one pump, optionally a pump 648 for the suction tube, and/or a pump 646 for the inflation tube. In some embodiments, the pumps are syringe pumps. Alternatively or additionally, the pumps have any another form known in the art. In the case of ambient air filling balloon 601, in some embodiments, only an inflation tube 666 and pump 646 are provided, and air leaving the balloon 601 is provided through a valve.

Optionally, the at least one pump is connected to at least one motor. Optionally, each of the suction pump 648 and the inflation pump 646 are in operable communication with motor 638 and motor 636, respectively. In some embodiments, motors 638 and 636 are controlled by a processor.

In some embodiments, pressure sensor 620 measures intracranial pressure, and in the case of pressure getting out of a predetermined range, the output of pressure sensor 620 leads to a cease of pumping fluid into or out of balloon 601. In some embodiments, the output of pressure sensor 620 reaches the same processor which is operable communication with motors 636 and 638.

In some embodiments of the invention, intracranial volume changing systems as shown in the above cited references may be used, after suitable modification, for example, to allow and provide the timing and volume features described herein, for carrying out some embodiments of the invention. For example, various balloon shapes as described may be used.

Also, it is noted that the description herein has focused on patients with high ICP. However, other cranial flow problems may be treated using the system and methods described herein, for example, such diseases as described in the above references. For example, methods and systems as described herein may be used to selectively, increase ICP or CPP at any part of the cycle, flatten ICP, provide venous squeezing, improve perfusion, improve outflow and/or other effects as described herein.

Deformable Catheter

Figure 7A:
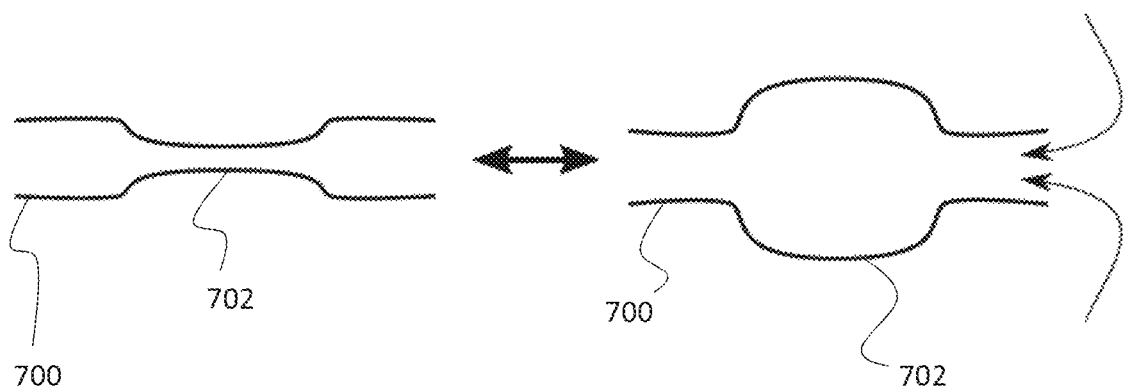

FIG. 7A shows an embodiment of a volume adaptor comprising a catheter 700, the catheter having an elastic and/or deformable portion 702. Optionally, a conformational change alternating an open and close configuration of the deformable portion, acts as a means for increasing and/or decreasing the volume of the cerebral compartment encompassing the catheter. For example, the catheter's deformable portion may deflate into the catheter inner lumen, increasing the volume of the surrounding compartment and optionally decreasing the ICP. Alternatively or additionally, the catheter's deformable portion may inflate to invade into the surrounding compartment, pushing into the tissue and potentially increasing ICP.

Fluid Propelling

Figure 7B:
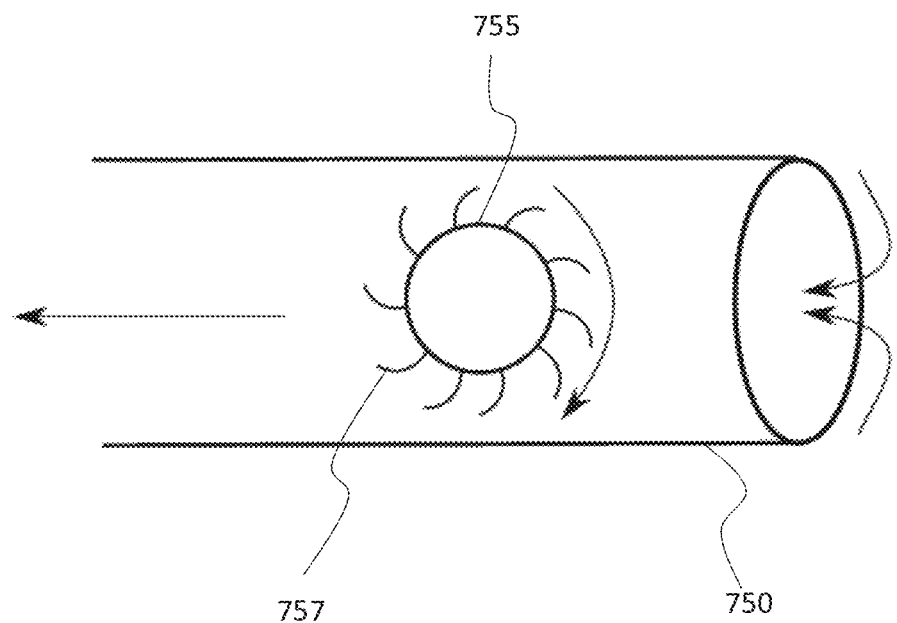

FIG. 7B shows an embodiment wherein fluid is propelled into a catheter 750 through actively rotating a wheel 755 having collecting elements 757, such as for example, an oar configured to resist fluid when across over it. Fluid entering into the catheter is drained from the cerebral compartment and/or from a balloon provided in the cerebral compartment, leading to reduced volume and to a reduced ICP.

Double Catheters

Figure 7C:
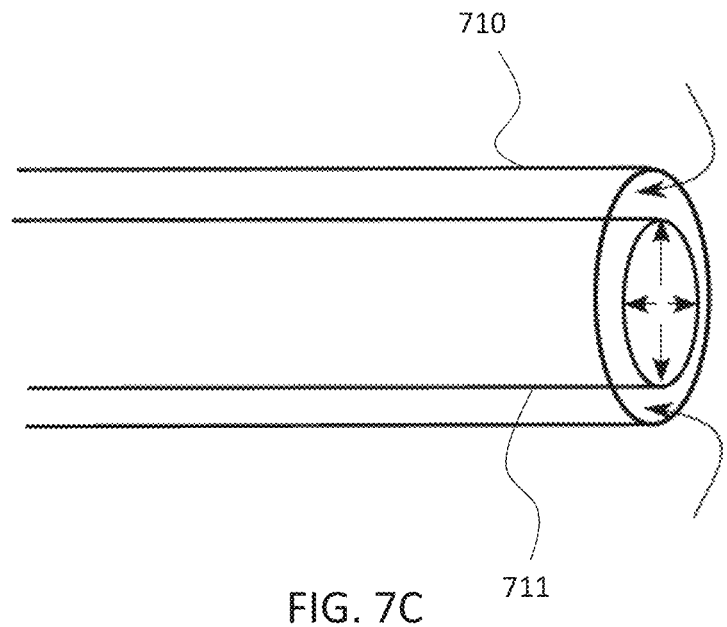

FIG. 7C shows an embodiment wherein a catheter 710 is provided surrounding a second inner catheter 711 having a smaller diameter. In some embodiments, the inner catheter comprises a fluid which exerts pressure radially outward, being proportional to the resistance to outflow. Optionally, the fluid of the inner catheter is modified by a processor having instructions to operate in synchronization with the cardiac cycle.

Figure 7D:
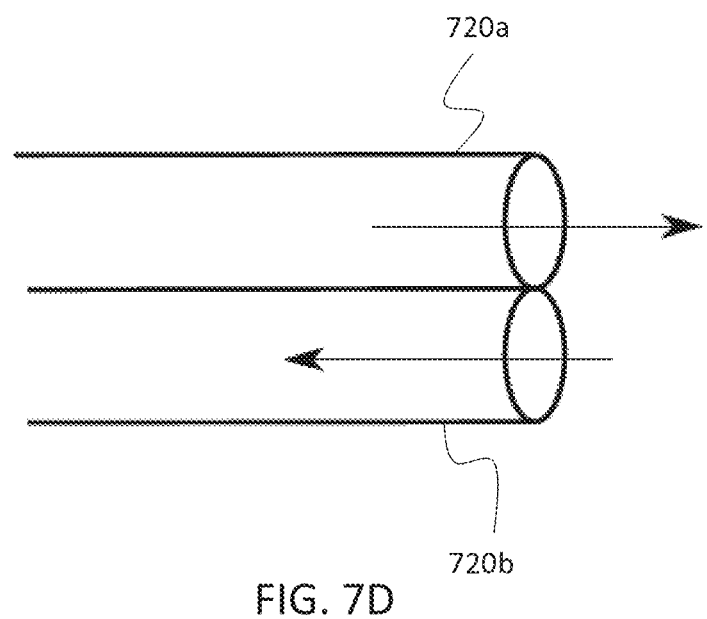

Reference is now made to FIG. 7D, illustrating a configuration of a double catheter wherein two catheters (or lumens, 720*a* and 720*b*) are provided side by side, in accordance with some embodiments of the present invention. In some embodiments, the ratio between the fluid volume of each lumen is controlled, optionally by an outer pump. In some embodiments, filling and draining the lumens is done simultaneously. Optionally, one lumen is designated for filling with fluid and the other lumen is designated for draining the lumens.

Craniectomy Placed Membrane

Figure 8:
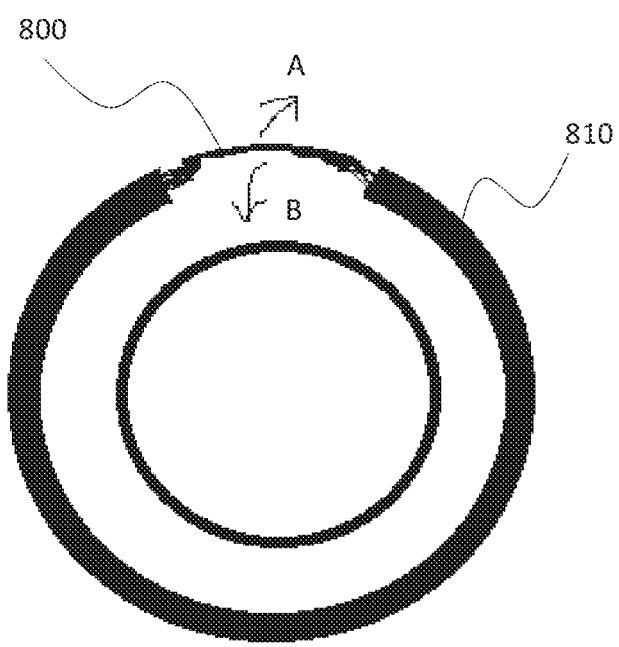
FIG. 8 illustrates an example of a volume adaptor in the form of a craniectomy and a membrane, in accordance with some embodiments of the invention.

FIG. 8 shows an embodiment wherein limited craniectomy is conducted in skull 810, followed by placing membrane 800 covering at least a portion of a cerebral compartment. Optionally, the membrane is flexible and/or resilient. In some embodiments, the membrane is controlled by a processor, optionally having instructions to relax and/or compress the membrane, causing it to move in the direction of A or B, respectively. In some embodiments, relaxing and/or compressing the membrane is executed in accordance with the cardiac cycle and/or according to ICP synchronous with the cardiac cycle.

Venous Sinus Balloon

Figure 9:
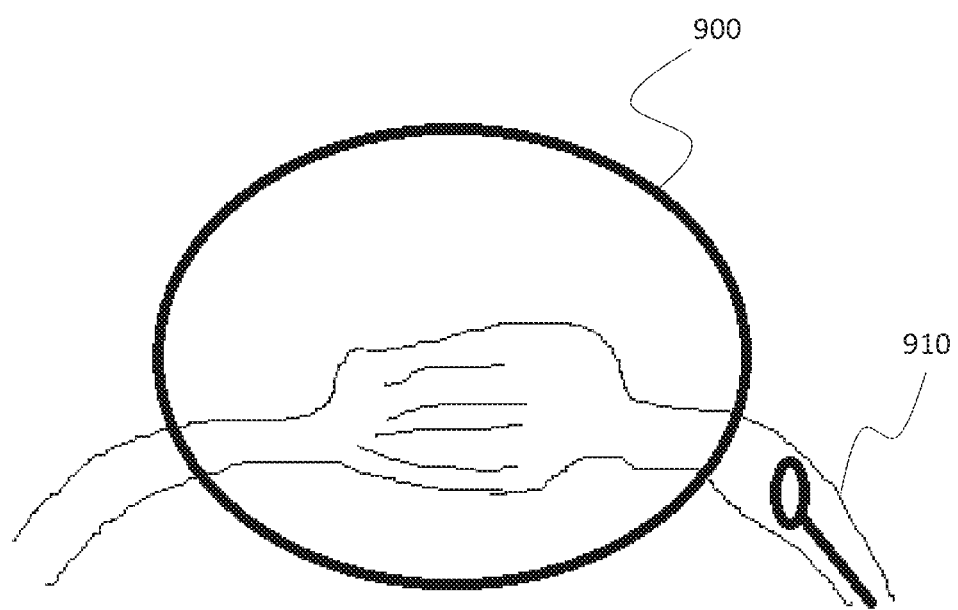
FIG. 9 illustrates an example of a venous volume adaptor, in accordance with some embodiments of the invention.

FIG. 9 shows a balloon 900 provided as a venous sinus balloon—a balloon at least partially inflated inside venous sinus 910, in accordance with some embodiments of the invention. In some embodiments, the venous balloon is gated to ECG, optionally inducing momentarily elevated and/or reduced venous pressure, potentially leading to a resistance to outflow, optionally a gradual resistance.

Volume Pressure Curve

In some exemplary embodiments of the invention, use is made of the ability to coordinate fluid volume change with ICP cycle. In one example, a pressure-volume curve can be generated by injecting fluid (into brain or into a, e.g., sealed, balloon in brain) at known times of the cycle. Optionally or alternatively, known fluid amounts are removed (or a balloon deflated) at known times in the cycle. In particular it is noted that timing can be coordinated to the extreme points of the cycle—peak systole and trough diastole.

Figure 10:
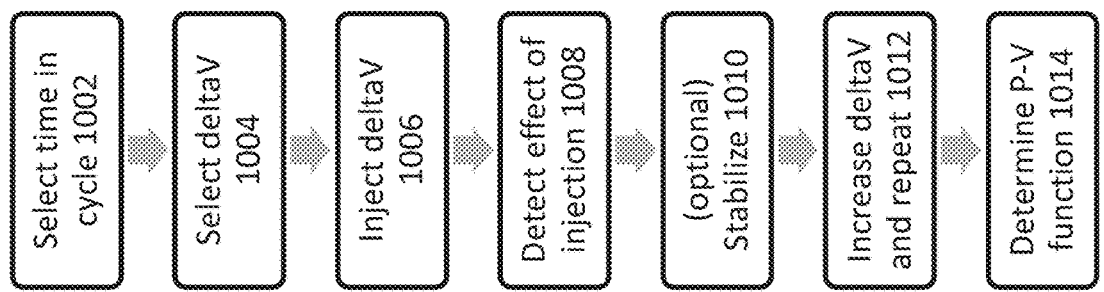
FIG. 10 is a flowchart of a method of determining a volume-pressure curve, in accordance with some embodiments of the invention.

FIG. 10 is a flowchart of a method of determining a volume-pressure curve, in accordance with some embodiments of the invention.

At 1002, a time in the cardiac cycle is selected, optionally an end diastolic time when the brain is maximally drained of blood.

At 1004, an amount to be injected (deltaV) is elected, for example, 0.1 cc.

At 1006 the deltaV is injected, for example, by inflating adapter 101 by test amount, for example, relative to previous activation or relative to a no-expansion baseline.

At 1008 the effect of the injection on, for example, ICP and/or other physiological parameters is detected.

At 1010, the brain is optionally allowed to stabilize at a new set point.

At 1012, deltaV is increased, for example, in fixed steps of 0.1 cc and the process is repeated.

At 1014 the responses of the brain are collected to define a V-P function which may also be used to indicate brain compliance. Optionally, the process may be repeated at other stages of the cardiac cycle, so as to, for example, obtain compliance under different blood-volume conditions.

In some exemplary embodiments of the invention, determining the compliance curve may be useful to calculate a compliance dP/dV could be calculated and the state of cerebral reserve and/or point of de-compensation can be evaluated. This may be helpful to differentiate between different disease states, for example, a patient with normal pressure but diminished reserve which are in higher risk and might need more aggressive treatment than one with higher pressure but larger reserves. This may also affect suggested treatment parameters, search start parameter and/or markers used to evaluate the treatment.

Figure 11:
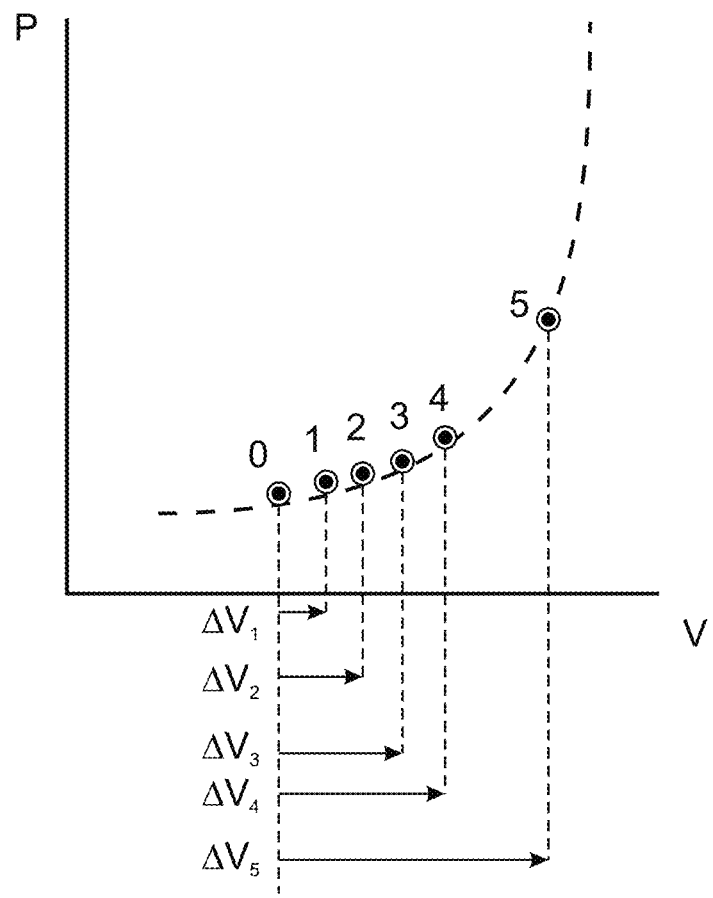
FIG. 11 is an example of a volume-pressure curve determined in accordance with some embodiments of the invention.

FIG. 11 shows an exemplary pressure volume curve. In this figure point 0 (e.g., trough diastole, where brain is most relaxed) is known exactly and consistently between cycles. A same deltaV (e.g., between 0.01 cc and 1 cc, for example, between 0.05 and 0.5 cc) are injecting at the same exact spot of the PV curve, yielding points 0-5 in the figure, so an operator or system can reconstruct a PV curve (dashed line) based on a simultaneously measured ICP.

General

It is expected that during the life of a patent maturing from this application many relevant syringe devices will be developed and the scope of the term syringe and/or cartridge is intended to include all such new technologies a priori.

As used herein the term "about" refers to ±25%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for increasing cerebral perfusion in a patient by repeatedly modifying a volume of a volume adaptor introduced into a cranial volume of said patient, said method comprising:
    estimating a timing of a systolic cerebral blood inflow which forms part of a cerebral blood flow cycle in a cardiac activity of said patient;
    shrinking the volume of said volume adaptor to a decreased volume state in synchronization to said estimated timing of said systolic cerebral blood inflow, to an amount sufficient to decrease an intracranial pressure in said cranial volume, such that a flow of said systolic cerebral blood inflow is increased; and
    increasing the volume of said volume adapter to an increased volume state relative to said decreased volume state, wherein the volume at the increased volume state is more than 20% higher than a volume at said decreased volume state over less than 30% of said cerebral blood flow cycle;
    wherein said increasing is performed at a delay after said shrinking is completed and is during an estimated or measured time of a diastole of said cerebral blood flow cycle, said delay allowing inflow of cerebral blood during the diastole with reduced resistance.

2. The method according to claim 1, further comprising estimating in said cardiac activity of said patient a timing of a cerebral blood outflow, and wherein said increasing is performed in synchronization to said estimated timing of said cerebral blood outflow, thereby increasing the intracranial pressure in said cranial volume, such that said cerebral blood outflow is enhanced.

3. The method according to claim 1, wherein said increasing is performed less than ⅓ of said cerebral blood flow cycle before said shrinking is performed.

4. The method according to claim 1, wherein said increasing is initiated prior to a timing of a cerebral blood outflow.

5. The method according to claim 1, wherein said expanded state lasts less than 200 milliseconds.

6. The method according to claim 1, wherein said increasing comprises increasing the volume of said volume adapter to increase less than a threshold ICP.

7. The method according to claim 1, wherein said shrinking is completed before 10 milliseconds after the systole of the cerebral blood flow cycle starts.

8. A method for increasing cerebral perfusion in a patient by repeatedly modifying a volume of a volume adaptor introduced into a cerebral ventricle of said patient, over several cranial pressure cycles, said method comprising:
    estimating a timing of a cerebral blood outflow in a cardiac activity of said patient;
    expanding the volume of said volume adaptor in synchronization to said estimated timing of said cerebral blood outflow, to an amount sufficient to increase an intracranial pressure in said cerebral ventricle, such that a flow of said cerebral blood outflow is increased, wherein said expanding occurs over less than 30% of a cerebral blood flow cycle such that said volume is in a reduced volume state over most of said cerebral blood flow cycle,
    wherein said expanding is performed at a delay after the end of a measured or estimated systole of said cerebral blood flow and starts after the beginning of an estimated or measured time of a diastole of said cerebral blood flow cycle, said delay allowing inflow of cerebral blood during the diastole with reduced resistance otherwise caused by said expanding.

9. The method according to claim 8, wherein said expanding is performed in a first 60% of the diastole of said cerebral blood flow cycle.

10. The method according to claim 8, wherein said expanding is performed in a last 37% of the diastole of said cerebral blood flow cycle.

11. A system for increasing cerebral perfusion in a brain of a patient, comprising:
    a volume adaptor having an expandable compartment sized and shaped to be introduced into a skull of the patient, said volume adaptor operable by switching between a shrunk state sized to significantly decrease intracranial pressure and an expanded state sized to significantly increase intracranial pressure;
    at least one sensor for measuring a physiologic output of said patient; and
    a processor in operating communication with said volume adaptor, and having instructions, executed by said processor, for:
        (i) predicting, according to said physiologic input, a timing of at least one of a cerebral blood inflow and a cerebral diastole;
        (ii) switching said volume adaptor into said shrunk state in synchronization with said timing of the cerebral blood inflow;

(iii) maintaining said volume adaptor in said expanded state for less than 30% of a duration of a cardiac cycle; and (iv) maintaining said volume adaptor in said shrunk state during a delay period including at least part of said cerebral diastole, wherein said processor is configured to apply said switching for at least 100 cardiac cycles out of 1000 consecutive cardiac cycles.

12. The system according to claim 11, wherein said processor further comprises instructions for predicting, according to said physiologic input, a timing of a cerebral blood outflow and switching said volume adaptor into said expanded state in synchronization with said timing of the cerebral outflow.

13. The system according to claim 11, comprising a pump operative to switch said volume adaptor from said shrunk state to said expanded state in less than 50 milliseconds.

14. The system according to claim 13, wherein said processor further comprises instructions for controlling an external ventricular drain in conjunction with activating said pump to provide said switching.

15. The system according to claim 13, further comprising a physiological sensor and wherein said processor further comprises instructions to adjust at least one operating parameter of said pump and/or at least one timing parameter in response to an input from said physiological sensor.

16. The system according to claim 15, wherein the processor further comprises instructions for continuously adjusting a set of operating parameters of the system in response to patient physiological response.

17. The system according to claim 15, wherein the at least one timing parameter comprises a portion of said delay period and wherein the at least one operating parameter of the pump comprises a volume of expansion.

18. The system according to claim 11, wherein said expandable compartment comprises a non-compliant wall.

19. The system according to claim 11, wherein said expandable compartment contains fluid.

20. The system according claim 11, wherein said volume adaptor has a maximal volume of between 3 and 6 cc (cubic centimeters).

21. The system according to claim 11, wherein said processor further comprises instructions for gradually expanding said volume adaptor to a first expanded state at times when pressure in said brain is lower.

22. The system according to claim 11, wherein controller said processor further comprises instructions for automatically identifying a set of initial operation parameters by trying out a series of parameter settings.

23. The system according to claim 11, wherein said processor further comprises instructions for automatically generating a pressure volume curve for determining compliance of said brain.

* * * * *